(12) United States Patent
Teoh et al.

(10) Patent No.: US 9,492,279 B2
(45) Date of Patent: Nov. 15, 2016

(54) BIOABSORBABLE PLUG IMPLANTS AND METHOD FOR BONE TISSUE REGENERATION

(71) Applicant: OSTEOPORE INTERNATIONAL PTE LTD., Singapore (SG)

(72) Inventors: Swee Hin Teoh, Singapore (SG); Kim Cheng Tan, Singapore (SG); Dietmar Hutmacher, Singapore (SG); Thiam Chye Lim, Singapore (SG); Jan-Thorsten Schantz, Singapore (SG); Ning Chou, Singapore (SG)

(73) Assignee: OSTEOPORE INTERNATIONAL PTE LTD., Singapore (SG)

( * ) Notice: Subject to any disclaimer, the term of this patent is extended or adjusted under 35 U.S.C. 154(b) by 33 days.

(21) Appl. No.: 14/223,737

(22) Filed: Mar. 24, 2014

(65) Prior Publication Data
US 2014/0358238 A1    Dec. 4, 2014

Related U.S. Application Data

(62) Division of application No. 10/579,946, filed as application No. PCT/SG2004/000380 on Nov. 22, 2004, now abandoned.

(60) Provisional application No. 60/524,278, filed on Nov. 21, 2003.

(51) Int. Cl.
*A61F 2/28*     (2006.01)
*A61L 31/00*   (2006.01)
(Continued)

(52) U.S. Cl.
CPC ............ *A61F 2/2875* (2013.01); *A61L 31/005* (2013.01); *A61L 31/06* (2013.01); *A61L 31/146* (2013.01);
(Continued)

(58) Field of Classification Search
CPC .................. A61F 2/875–2002/2889; A61F 2/3099–2002/30998
See application file for complete search history.

(56) References Cited

U.S. PATENT DOCUMENTS

| | | | |
|---|---|---|---|
| 5,306,311 | A | 4/1994 | Stone et al. |
| 5,383,932 | A | 1/1995 | Wilson et al. |

(Continued)

FOREIGN PATENT DOCUMENTS

| | | |
|---|---|---|
| JP | 5-237137 | 9/1993 |
| JP | 5-84306 | 11/1993 |

(Continued)

OTHER PUBLICATIONS

Hutmacher et al., ("Design and Fabrication of a 3D Scaffold for Tissue Engineering Bone", as published in Agrawal et al., Eds Synthetic Bioadsorbable Polymers for Implants'. ASTM, West Conchohocken, PA; May 2000, pp. 152-167).*

(Continued)

*Primary Examiner* — Christopher D Prone
(74) *Attorney, Agent, or Firm* — Heslin Rothenberg Farley & Mesiti P.C.; Victor A. Cardona, Esq.

(57) ABSTRACT

A bioabsorbable plug implant, suitable for bone tissue regeneration, includes a first portion, and a second portion extending outwardly from the first portion, the first and second portions formed from expandable material. A method for bone tissue regeneration includes providing a bioabsorbable plug implant, wherein the implant has a first portion and a second portion extending outwardly from the first portion. The first and second portions are formed from expandable material. The second portion is inserted into a defect or gap of a bone. The first surface engages the outside contour of the defect or gap. The plug implant is allowed to contact body fluids, thereby expanding the size of the plug implant so that the plug fits into the defect or gap.

11 Claims, 36 Drawing Sheets

(51) Int. Cl.
A61L 31/06 (2006.01)
A61L 31/14 (2006.01)
A61M 27/00 (2006.01)
A61F 2/30 (2006.01)

(52) U.S. Cl.
CPC ............ *A61L 31/148* (2013.01); *A61M 27/00* (2013.01); *A61F 2002/2817* (2013.01); *A61F 2002/2839* (2013.01); *A61F 2002/3021* (2013.01); *A61F 2002/30062* (2013.01); *A61F 2002/30075* (2013.01); *A61F 2002/30113* (2013.01); *A61F 2002/30153* (2013.01); *A61F 2002/30154* (2013.01); *A61F 2002/30225* (2013.01); *A61F 2002/30233* (2013.01); *A61F 2002/30691* (2013.01); *A61F 2002/30914* (2013.01); *A61F 2002/30915* (2013.01); *A61F 2002/30971* (2013.01); *A61F 2210/0004* (2013.01); *A61F 2210/0061* (2013.01); *A61F 2230/0006* (2013.01); *A61F 2230/0019* (2013.01); *A61F 2230/0021* (2013.01); *A61F 2230/0067* (2013.01); *A61F 2230/0069* (2013.01); *A61F 2310/00005* (2013.01); *A61L 2430/02* (2013.01)

(56) References Cited

U.S. PATENT DOCUMENTS

| | | | | |
|---|---|---|---|---|
| 5,503,164 | A * | 4/1996 | Friedman | A61B 17/8085 128/897 |
| 5,607,474 | A * | 3/1997 | Athanasiou et al. | A61F 2/28 623/23.71 |
| 5,899,939 | A * | 5/1999 | Boyce et al. | A61F 2/28 523/113 |
| 2002/0028243 | A1 | 3/2002 | Masters | |
| 2002/0032488 | A1 | 3/2002 | Brekke et al. | |
| 2002/0183858 | A1 | 12/2002 | Contiliano et al. | |
| 2003/0100947 | A1 | 5/2003 | Nadler et al. | |
| 2003/0220700 | A1 | 11/2003 | Hammer et al. | |
| 2007/0083268 | A1 | 4/2007 | Teoh et al. | |

FOREIGN PATENT DOCUMENTS

| | | |
|---|---|---|
| JP | 6-3611 | 2/1994 |
| JP | 9173435 | 7/1997 |
| JP | 9-290026 | 11/1997 |
| JP | 3-126113 | 10/2006 |
| WO | WO9315682 | 8/1993 |
| WO | WO0143667 A1 | 6/2001 |
| WO | WO 0160288 A1 | 8/2001 |

OTHER PUBLICATIONS

Broaddus W. C. et al. "Titanium miniplates or stainless steel wire for cranial fixation: a prospective randomized comparison", J. Neurosugr., 96(2): 244-247, 2002.
Winkler, P. A. et al. "Foreign-body reaction to silastic burr-hole covers with seroma formation: Case report and review of the literature", Pathol Res Pract., 196(1): 61-66, 2000.
Habal M. B. and Pietrzak W. S. "Key points in the fixation of the craniofacial skeleton with absorbable biomaterial", J Craniofac Surg., 10(6): 491-499, 1999.
Stendel R. et al. "Biodegradable implants in neurosurgery", Acta Neurochir (Wein), 143(3): 237-243, 2001.
Schantz J-T et al. "Repair of calvarial defects with customized tissue-engineered bone grafts I. Evaluation of osteogenesis in a three-dimensional culture system", Tissue Engineering 9 (Sup 1), 113-126, 2003.
Schantz J-T et al. "Repair of calvarial defects with customized tissue-engineered bone grafts II. Evaluation of cellular efficiency and efficacy in vivo", Tissue Engineering 9 (Sup 1), 127-139, 2003.
Yamashima T. "Modern cranioplasty with hydroxylapatite ceramic granules, buttons, and plates", Neurosurgery, 33 (5): 939-940, 1993.
Miyake H. et al. A new technique for cranioplasty with L-shaped titanium plates and combination ceramic implants composed of hydroxyapatite and tricalcium phosphate (ceratite), Neurosurgery, 46(2): 414-418, 2000.
Koyama J. et al. "A newly designed key-hole button" J Neurosurg., 93(3): 506-508, 2000.
Emonds N. and Hassler W. E. "New device to treat chronic subdural hematoma—hollow screw", neurol Res., 21 (1): 77-78, 1999.
Hutmacher D. W. et al. "Mechanical properties and cell cultural response of polycaprolactone scaffolds designed and fabricated via fused deposition modeling", J Biomed Mater Res., 55(2): 203-216, 2001.
Caplan A. I. and Bruder S. P. "Cell and molecular engineering of bone regeneration", Principles of Tissue Engineering, 603-618, 1997.
Nieden N. I. et al. "In vitro differentiation of embryonic stem cells into mineralized osteoblasts", Differentiation, 71: 18-27, 2003.
Rohner D. et al. "In vivo efficacy of bone-marrow-coated polycaprolactone scaffolds for the reconstruction of orbital defects in the pig", J Biomed Res., 574-580, 2004.
Japanese Office Action for corresponding JP Application No. 2006-541104 dated Mar. 18, 2011, with English Translation.
Cao et al., "Scaffold Design an in Vitro Study of Osteochondral Coculture in a Three-Dimensional Porous Polycaprolactone Scaffold Fabricated by Fused Deposition Modeling", Tissue Engineering, vol. 9, Suppl. 1, 2003, pp. S-103-S-113.
Feb. 10, 2012 Office Action for co-pending European Patent Application No. 04800445.1.
Supplemental Partial European Search Report for corresponding European Application No. 04800445.1, completed Nov. 10, 2008.
Jun. 29, 2010 Office Action for corresponding Indian Application No. 724MUMNP/2006.

* cited by examiner

Fig. 3

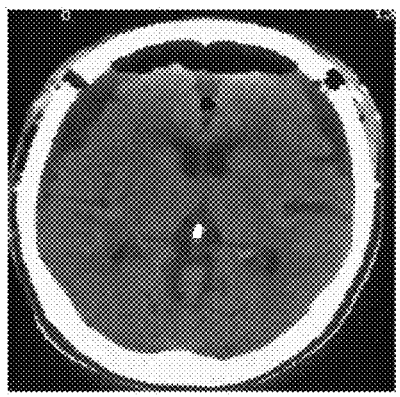
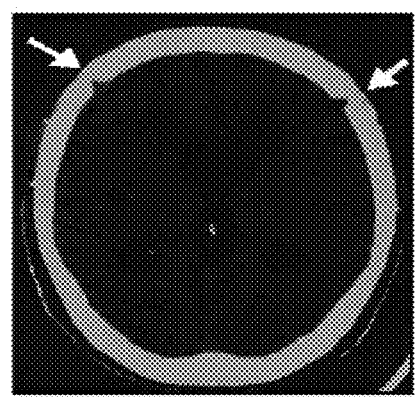
FIG. 8A
FIG. 8B (from Figure 30A)

BIOABSORBABLE PLUG IMPLANTS AND METHOD FOR BONE TISSUE REGENERATION

CROSS REFERENCE TO RELATED APPLICATIONS

This application is divisional of U.S. patent application Ser. No. 10/579,946 filed on May 22, 2006, which is a 371 national stage of PCT International Application No. PCT/SG2004/000380, filed on 22 Nov. 2004, and published in English on 2 Jun. 2005, as WO 2005/048885 A1, U.S. patent application Ser. No. 10/579,946 filed on May 22, 2006 also claims priority to U.S. Provisional Application Ser. No. 60/524,278, filed 21 Nov. 2003. The entire disclosures of the above-referenced applications are incorporated herein by reference.

FIELD OF THE INVENTION

The present invention relates to an expandable bioabsorbable implant for bone tissue regeneration and to a method for bone tissue reparation and regeneration.

BACKGROUND OF THE INVENTION

The reconstruction of bones, for example of the skull, has been an ongoing intensive research. With reference to the skull reconstruction, whereas several reports focus on the reconstruction of large and complex-shaped cranial defects comparatively little has been reported about restoration of small but cosmetically undesirable osseous gaps in trephined burr holes. Trephination burr holes often result in small but undesirable scalp and skin depression. Subdural hematoma is a common problem especially if patient has head injuries related to accidents or due to blood clogging in the brain as a result of stroke. It is usually treated by burr hole drainage or irrigation. The trephined burr hole procedure involves drilling a hole typically 14 to 19 mm in diameter on to the patient's skull.

Various bone grafts or bone substitute materials have been used to fill those defects which normally do not enable the bone to regenerate and recover the defect. Tessier (Tessier 1982) has reported the use of split calvarial autologous grafts to bridge or fill defects. This technique represents a cheap and straight forward approach however sometimes the primary incision has to be extended in order to harvest the graft from the surrounding calvarial bone. However, there are problems associated with the use of bone tissue grafts. If the patient's own bone is used as a graft, a surgeon must perform an additional, traumatic operation to take the bone sample. If the bone graft is taken from another person or animal bone is used, viral contaminations or immunological problems are possible, even if the graft is treated to make it compatible with the patient's tissue.

Another possibility using autologous graft material is to collect the bone dust during the craniotomy procedure and mix it with a hydrogel like fibrin glue and use that paste to fill out the defect after the procedure (Matsumoto, 1998).

Cranioplastic materials based on metal have been extensively used in the form of titanium plates and meshes. The high biocompatibility and mechanical strength in combination with the easy handling and accurate fixation thus might justify the relatively high costs (Broaddus, 2002). Silastic, a commonly used biomaterial in medicine is also used as burr hole cover however controversy discussed in terms of its biocompatibility as reports indicate the formation of foreign body reaction due to pathologic tissue response to its elastomers (Winkler 2000).

In recent years there is a move towards osteoinductive biomaterials and implants which allow the ingrowth of bone tissue and therefore better integration of the implants. The trend using bioresorbable materials and tissue engineering has resulted in protheses which are eventually replaced by autologous bone (Habal 1999, Stendel 2001, Schantz 2003a, b). Kobayashi et al (1987) have designed and fabricated various alumina ceramic implants to reconstruct trephination burr holes and to prevent postoperative dents in the skin. Ceramic implants based on hydroxyapaptite are increasing popular due to their mechanical properties, osteoinductive and integrative characteristics (Yamashina, 1989, 1993, Miake, 2000), Yamashina has designed hydroxyapatite plates which are domed and elliptic in shape so that they fit the convexity of the occipital region. The author has also designed HA-buttons to fit burr hole defects as well as apatite granules for linear skull defects. A specially designed "key-hole button" based on hydroxyapatite was designed by Koyama et al (2000) for trephination defects.

Various surgical approaches and implantable device have been developed especially for the treatment of acute or chronic subdural hematomas associated burr hole defects. In these cases it is often desirable to place a shunt or catheter to monitor or drain intra or pericranial fluid and parallely to monitor pressure characteristics. Emonds and Hassler have developed a hollow screw which allows placement of a catheder (1999) whereas Dujovny et al (2002) designed a burr hole cover for a hydrocephalus shunt drainage based on titanium consisting of a circular plate with five attached flaps for screws and a key hole like opening.

U.S. Pat. No. 6,350,284 ('284) describes a bioabsorbable cranial implant consisting of a rigid plate and a fibrous web layer containing pores between 30 and 1000 µm in diameter. This implant, however, requires to be fixed to the bone by means for attachment, for example, sutures, tacks, or screws, and it is therefore not practical.

SUMMARY OF THE INVENTION

The present invention addresses the problems above and, in particular, provides new and improved implant, suitable for tissue bone regeneration and bone restoration, easy to be use and which does not require means for attachment to the bone. Tissue bone regeneration of an osseous defect or gap can be partial or complete; in the latter case, for the purpose of the present application it will be indicated as bone restoration.

In particular, the present invention discloses a bioabsorbable plug implant suitable for bone tissue regeneration, wherein the implant comprises a first portion, and a second portion extending outwardly from the first portion, the first and second portions formed from expandable material.

The plug implant of the invention may have any shape suitable to be inserted into a defect of a bone, for example: the plug implant may be shaped like a cone, truncated-cone, a pentahedron, a truncated-pentahedron, and/or a button mushroom.

According to a particular aspect of the plug implant of the invention, the first portion comprises a first surface, and the second portion comprises a second surface, opposite to the first, the first surface having an area smaller than the area of the second surface. The first and the second surfaces of the plug implant may have circular, square or rectangular shapes. The first and second surfaces may be plane surfaces.

According to one embodiment, the plug implant of the invention has a tapered shape.

According to another embodiment, the plug implant comprises a the first portion having a thickness X, and the second portion having a thickness Y, the ratio X:Y being from 1:1 to 10:1.

The plug implant of the invention is made of a material which expands in contact with hydrophilic solution, hydrophilic liquid and/or body fluid.

The expandable material may be formed from porous material.

The plug implant of the invention may preferably be made of an expandable material comprising bioresorbable polycaprolactone (PLC). For example, 20% TCP-PCL. The plug implant may be prepared by layering PLC filaments layer by layer using, for example, the Fused Deposition Modeling (FDM) technology.

The PLC filament layers of the plug implant may have an orientation of 0 degree, 60 degree and/or 120 degree.

According to a further embodiment, the plug implant comprises an opening for placement and removal of a catheter for drainage.

In particular, the plug implant is suitable to be inserted into a defect or a gap of a bone and the plug implant does not require means for fixing the plug to the external surface of the bone.

The plug implant may further comprise a bioactive agent.

The invention further provides a method for bone tissue regeneration comprising the steps of:
  providing a bioabsorbable plug implant, wherein the implant comprises a first portion and a second portion extending outwardly from the first portion, the first and second portions formed from expandable material;
  inserting the second portion into a defect or gap of a bone, the first surface engaging the outside contour of the defect or gap;
  allowing the plug implant to contact body fluids, thereby expanding the size of the plug implant so that the plug fits into the defect or gap.

In the method of the invention, the implant may comprise a first and a second surface, opposite to each other, the first surface having an area smaller than the area of the second surface.

In the method of the invention, the plug implant may be formed from a porous material allowing the bone cells to penetrate into the plug implant and to regenerate the bone tissue.

The method may be used for any bone tissue regeneration. For example, it may be a method for performing cranioplasty.

In the method of the invention, the plug implant is inserted into a defect of the bone, in a way that the plug implant and the bone defect have an initial tolerance of less than 1 mm, less than 0.5 mm, or less than 0.2 mm.

The method according to the invention can be used for therapeutic treatment of restoration of osseous defects or can be used for non therapeutic treatment for the cosmetic restoration of undesirable osseous gaps.

The method can be applied for the bone tissue regeneration and/or osseous restoration.

BRIEF DESCRIPTION OF THE FIGURES

Figure 3:
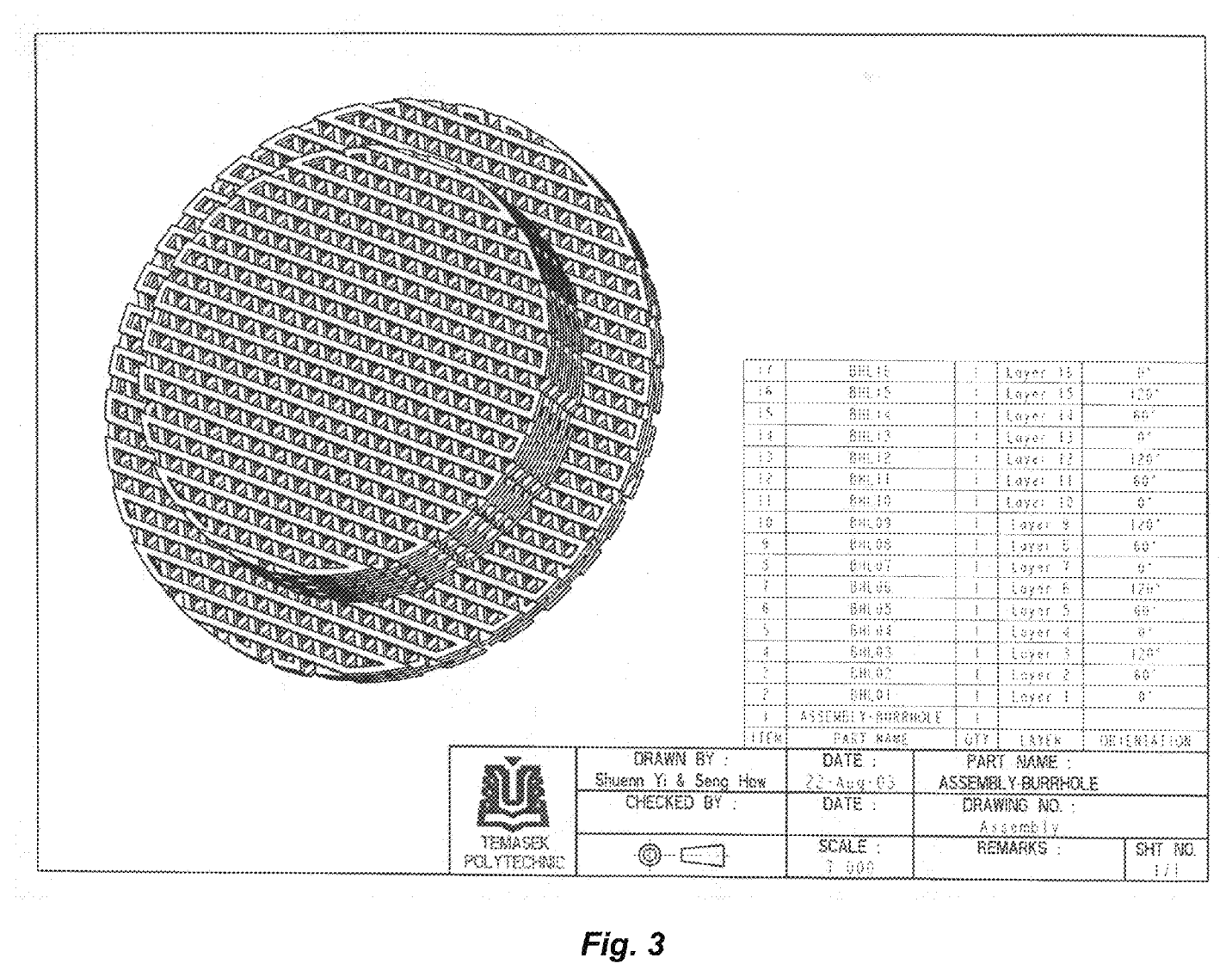

FIG. 3 is an isometric view of the case 1 Burr Plug (2) design of FIG. 2.

FIGS. 8A and 8B show one wk postoperative CT showing the two bur holes in FIG. 8A (Left); after 3 mth postoperative CT Implants were well integrated and started to mineralise in FIG. 8B (Right) on human subjects.

FIG. 15B depicts a side view showing cell sheets covering the scaffolds and collagen fibers formed after three weeks in vitro culture under induction.

DETAILED DESCRIPTION OF THE INVENTION

Bibliographic references mentioned in the present specification are for convenience listed in the form of a list of references and added at the end of the examples. The whole content of such bibliographic references is herein incorporated by reference.

One aspect of the present invention relates to construction of bioresorbable plug implant suitable for bone tissue regeneration. Tissue bone regeneration of an osseous defect or gap can be partial or complete: in the latter case, for the purpose of the present application it will be indicated as bone restoration.

The bioresorbable plug implant and method for bone tissue regeneration can be applied to any type of osseous defect or gaps. A particular application of the plug implant of the invention is for example cranioplasty.

The implant according to the invention has the shape of a plug. For the purpose of the present invention, a plug implant suitable for bone tissue regeneration and/or bone restoration is defined as an implant which fits substantially tightly into a bone defect or gap, for example a bone hole, used to fill the defect or gap or act as a wedge or stopper. For the purpose of the present invention a defect or a gap refer to a cavity of the bone. With the term defect it is referred a condition which may be considered a disease and needs to be treated therapeutically, whilst with the term gap it is referred to a condition which is not a disease and may be treated non therapeutically for cosmetic purpose. For the purpose of the present application, the term "burr hole" will be used to generally indicate the defect and/or gap. The plug implant of the invention may also be addressed as "burr plug". The structure of the expandable material from which the plug implant is made may also be indicated as "scaffold".

In particular, the present invention discloses a bioabsorbable plug implant suitable for bone tissue regeneration, wherein the implant comprises a first portion, and a second portion extending outwardly from the first portion, the first and second portions formed from expandable material.

The plug implant of the invention may have any shape suitable to be inserted into a defect of a bone, for example, the plug implant may be shaped like a cone, truncated-cone, a pentahedron, a truncated-pentahedron, and/or a button mushroom.

According to a particular aspect of the plug implant of the invention, the first portion comprises a first surface, and the second portion comprises a second surface, opposite to the first, the first surface having an area smaller than the area of the second surface. The first and the second surfaces of the plug implant may have circular, square or rectangular shapes. The first and second surfaces may be plane surfaces.

The plug implant of the invention is made of a material which expand in contact with hydrophilic solution, hydrophilic liquid and/or body fluid.

Figure 1:
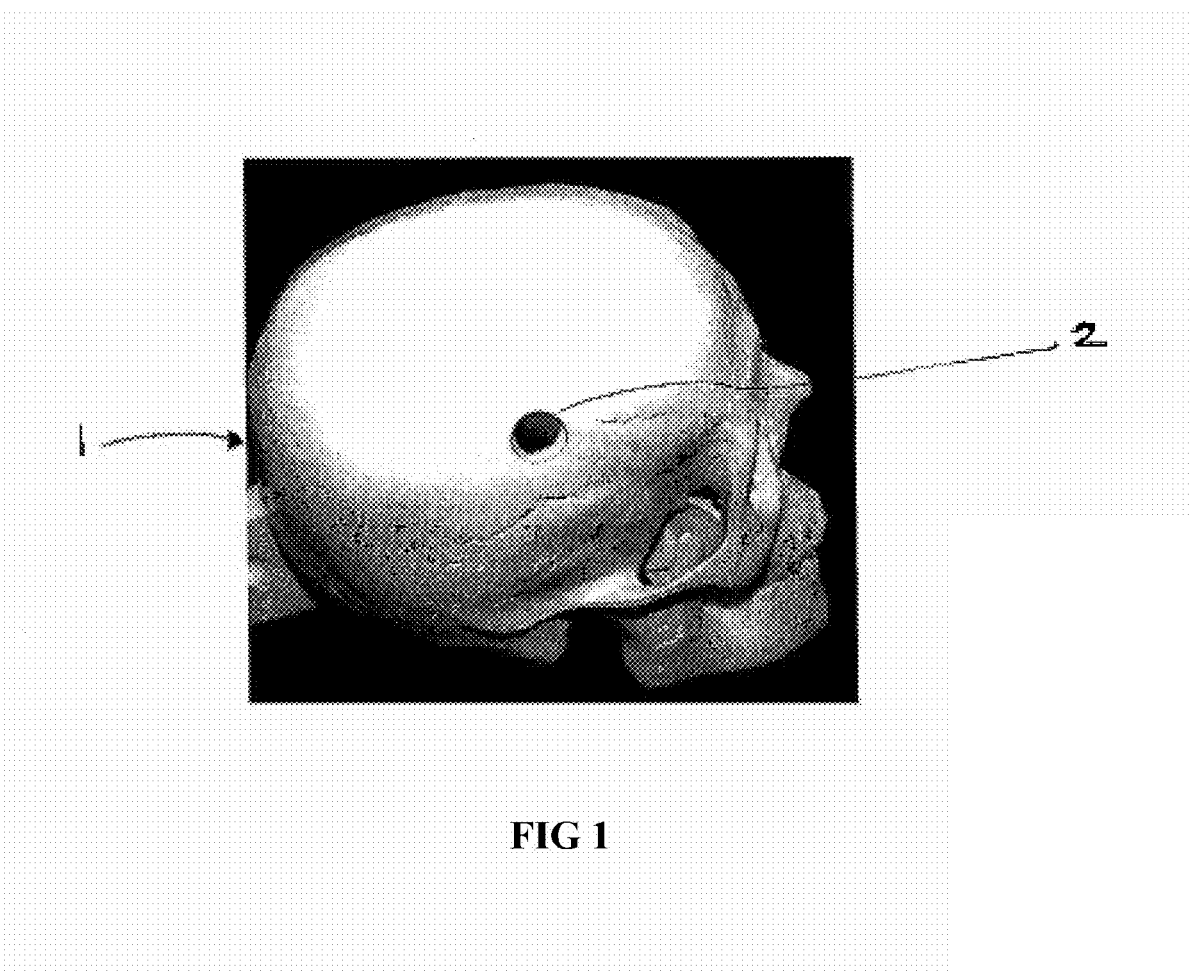
FIG. 1 show a typical burr hole or defect (2) created for drainage/irrigation and neurological examination on a phantom skull (1).

FIG. 1 show a skull (1) phantom comprising a burr hole (2), which for the purpose of the invention may be distinguished as defect (2) or gap (2).

With reference to FIG. 1, which demonstrates an embodiment of the present invention, the plug implant can be shape like a "button mushroom" (3), comprising a first portion (5), and a second portion (4) extending outwardly from the first portion, the first and second portions formed from expandable material. The plug implant of the invention however is not limited to the shape of a button mushroom but may have any shape suitable to be inserted into a defect of a bone, for example, the plug implant may be shaped like a cone, truncated-cone, a pentahedron, a truncated-pentahedron, and/or a button mushroom.

More in particular, in the embodiment exemplified in FIG. 1, the first portion (5) comprises a first surface (5), and the second portion (4) comprises a second surface (4), opposite to the first, the first surface having an area smaller than the area of the second surface. In FIG. 1, the first and the second surfaces of the plug implant have circular shapes. The first and second surfaces have plane surfaces. However, the shape is not limited to a circular one, but may be for example, a square or rectangular shape. Similarly, the surfaces is not limited to a place surface but may have any surface suitable for the purpose of the present invention, for example, an irregular, conical, acute, or elliptical shape may be within the scope of the present invention.

The first and second portions may also be characterized according to their thickness. In particular, the first portion (5) comprises the first surface and has a thickness X, whilst the second portion (4) comprises the second surface and has a thickness Y, the ratio X:Y being from 1:1 to 1:10. More in particular, in FIG. 1, the ratio X:Y is 11:4, that is, the first portion (5) comprises 11 layers, whilst the second portion (4) comprises 4 layers. The number of layers may be chosen by the skilled person according to the particular shape of the plug implant and according to the type of bone, burr hole, and particular conditions of the patient, human or animal. As a particular example, the plug implant can be designed in such a way to such that a second portion may have thickness of 1 mm and the first portion thickness 3 mm.

Figure 2:
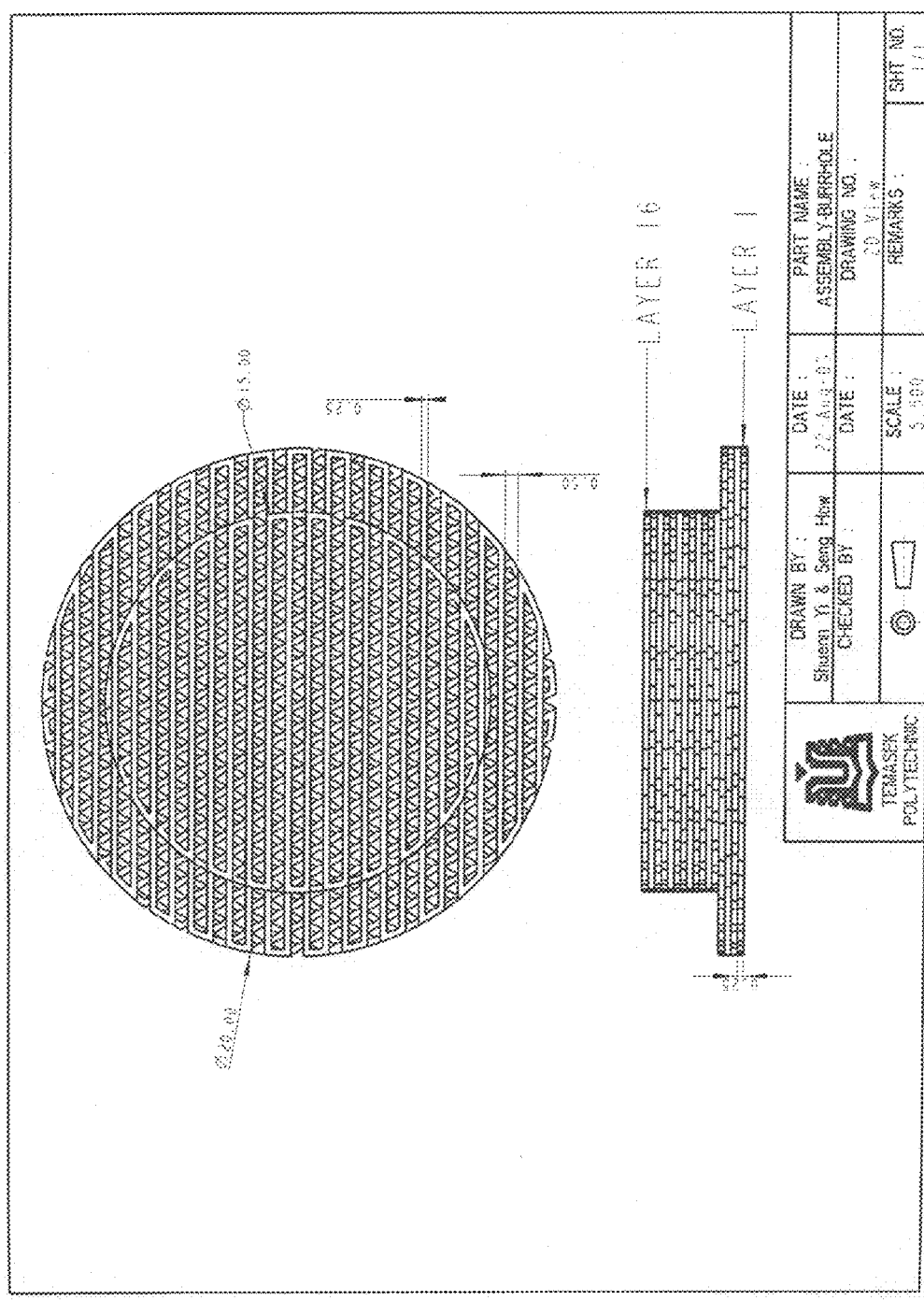
FIG. 2 is an orthographic view of Case 1 Burr Plug (3) design. The plug implant (3) comprises a first or upper surface (5) and a second of lower surface (4).
Figure 4A:
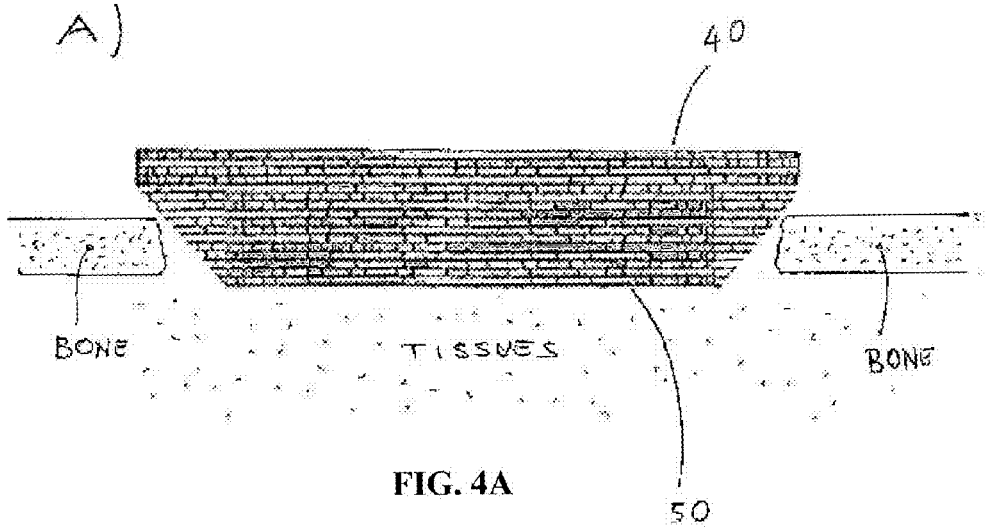
FIG. 4A shows an embodiment wherein the first or lower surface (50) of the plug implant (30) is inserted into a defect of the bone, and wherein the plug implant has a tapered shape.
Figure 4B:
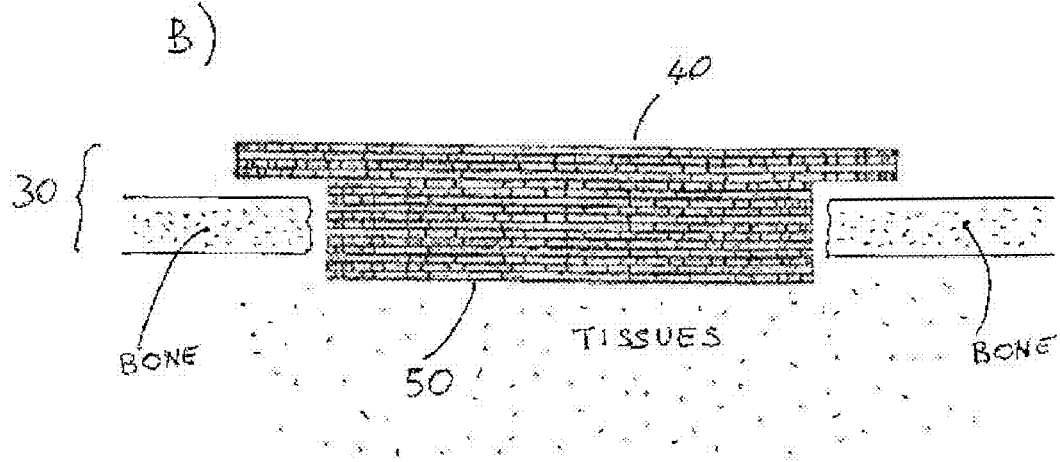
FIG. 4B shows the embodiment of FIGS. 2 and 3.

FIG. 2 is an isometric view of the embodiment of FIG. 1. More in particular, FIG. 2 shows the layered-scaffold structure made formed from biodegradable polymer filaments.

According to a further embodiment, the plug implant of the invention has a tapered shape or may have any shape suitable to be inserted into a defect of a bone, for example, the plug implant may be shaped like a cone, truncated-cone, a pentahedron, a truncated-pentahedron, and/or a button mushroom.

FIG. 2(A) shows a plug implant having a tapered shape comprising a first portion (50) comprising a first surface (50), and the second portion (40) comprising a second surface (40), opposite to the first surface, the first surface (50) having an area smaller than the area of the second surface (50). The first portion (50) plug implant is inserted into the bone defect or gap whilst the second portion (40) engages with the contour of the defect or gap avoiding the plug implant to penetrate into the bone cavity.

The first and the second surfaces of the plug implant may have circular, square or rectangular shapes. The first and second surfaces may be plane surfaces.

FIG. 2(B) shows the embodiment of FIGS. 1 and 2.

The size of the plug implant according to any embodiment of the invention as well as the first and second portion can be chosen by the skilled person according to the size of the bone defect or gap. For example, the plug implant can be designed in such a way to such that a second portion may have a thickness of 1 mm and the first portion a thickness 3 mm. The plug implant may have for example a diameter of the first portion of 15 mm and the diameter of the second portion of 20 mm (see FIGS. 1 and 2).

The particular shape of the plug of the invention in combination with the material which is a material which is expandable or swell (for example polycaprolactone (PCL)) at contact with at contact with hydrophilic solution, hydrophilic liquid and/or body fluid allows the plug implant to 'snap fit' into the defect or gap without the need of means for attaching the plug to the bone. The plug implant of the invention therefore can be used without requiring means for attachment like screws, which are instead used for titanium plates for cranioplasty or which are necessary for the implant described in U.S. Pat. No. 6,350,284. Accordingly, the plug implant of the invention does not require holes for insertion of means for attachment to the bone surface, like screws. The absence of screws meant one important advantage—it allows an easy placement of the burr plug in the shortest possible time.

More in particular, initial tolerance of no more than 1.0 mm, no more than 0.5 mm or no more of 0.2 mm between the plug implant and the defect or gap on the bone (for example, on the cranium), allows the 'snap fit' design to operate effectively. The larger second portion (the "top cap") ensures that the plug implant remains in the contoured position of the defect or gap of the bone not accidentally pushed too far below the thickness of the bone of the structure (for example, of the skull).

Furthermore, the expandable material may be of porous material, for example 20% TCP-PCL. More in particular, 20% TCP-PCL with 60-70% of porosity. Preferably, 20% TCP-PCL with 65% of porosity. This also allows the plug implant to better fitting within the defect or gap contour due to the elastic compressibility of the porous structure. It will be appreciated that a rigid structure, like the one described in U.S. Pat. No. 6,350,284 does not have such a capability. The scaffolds of the plug implant may have a completely interconnected porous architecture and a porosity of approximately 60 to 70%. This morphology allowed cells to be trapped and proliferate when the scaffolds are implanted in the body (Hutmacher et al, 2001).

Figure 5A:
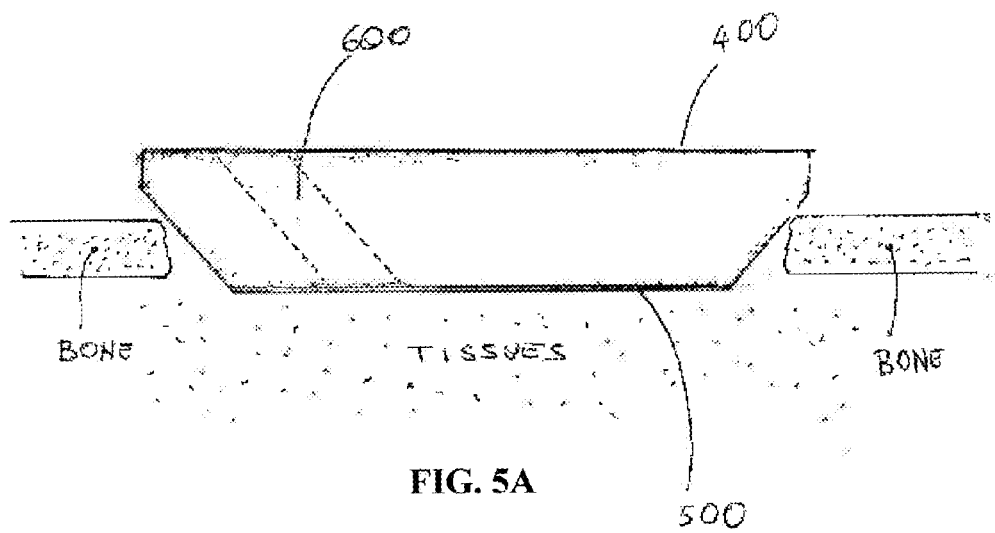
FIGS. 5A and 5B show the embodiments of FIGS. 4A and 4B, further comprising an opening for the insertion and/or removal of a catheter for drainage.
Figure 5B:
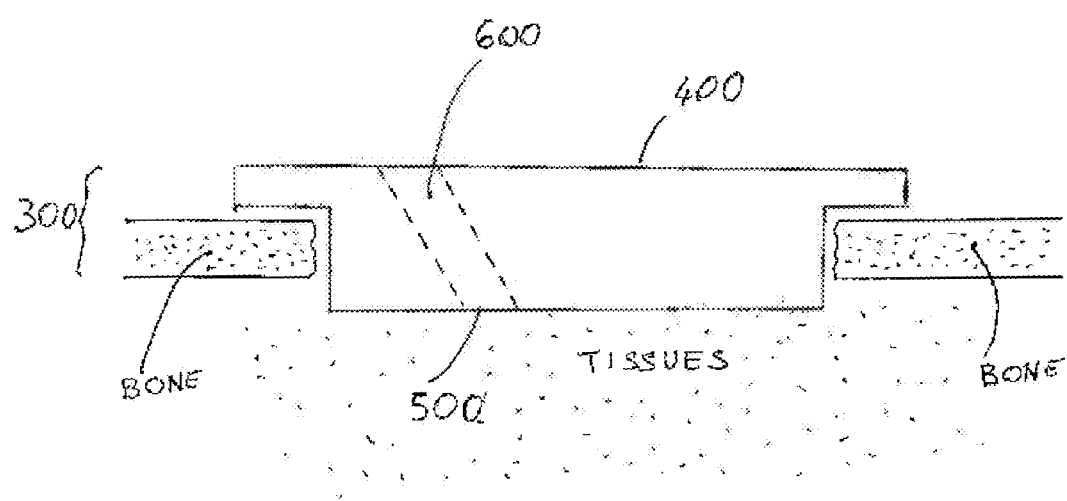
Figure 7:
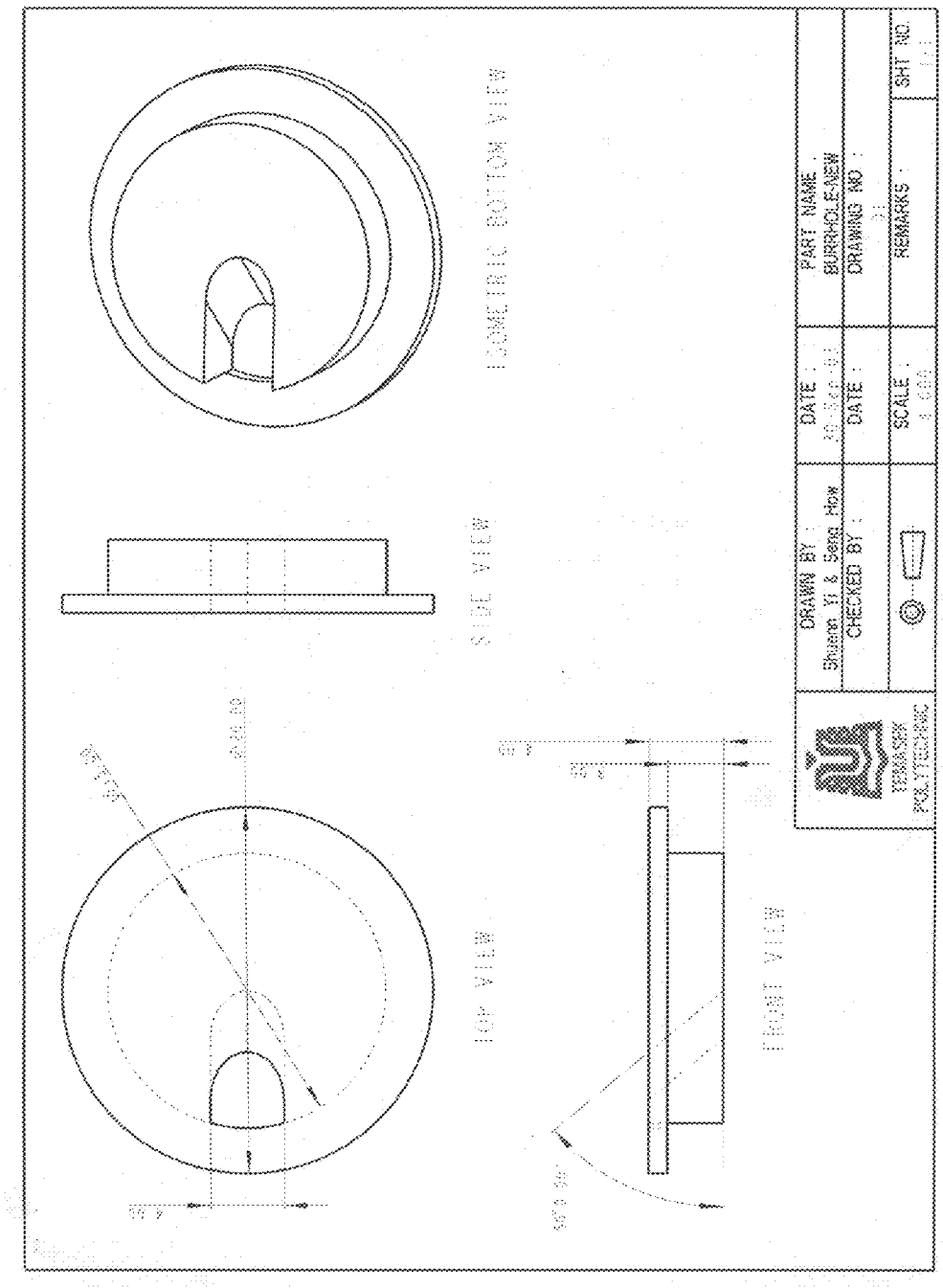
FIG. 7 is an orthographic and isometric view of the Case 2 Centre Hole Burr Plug Design that allows easy placement and removal of a catheter.

FIGS. 5 (A) and (B) and FIG. 7 show a further embodiment wherein the plug implant comprises and opening (600, 610) for placing catheter for performing drainage. This design allows an easy placement and removal of a catheter which can be inserted at an angle in the scaffold for drainage purposes.

Any bioabsorbable material known in the art suitable for the construction of the plug implant of the present invention can be used. For example, any bioabsorbable polymer or copolymer can be used. In particular, a bioresorbable polycaprolactone (PCL) polymer which has been proven to be biocompatible, degrades slowly and allows bone cells to attach and proliferate, has been proven particularly suitable for the purpose of the present invention. With time the cells expressed they own extra cellular matrices and bone like structures results as the PCL is reabsorbed and metabolised by the body. TCP-PCL (20% weight per volume) hybrid scaffold using a solid-free form fabrication technology, known as fused deposition modeling (FDM), in combination tricalcium phosphate (TCP) with PCL may be prepared according to (Dennis et al., 2003). More in particular, 20% TCP-PCL having 60-7-% of porosity, preferably 65% of porosity may be used. Most importantly, the computer-controlled FDM process permits the design and fabrication of porous scaffolds with suitable mechanical strength that mimics the in vivo bone architecture. The approach embraces the concept of tissue engineering. The scaffold design of the plug implant may be constructed according to any methodology known in the art. For example, by layering of PCL filaments layer by layer via a rapid prototyping process, like the so called "Fused Deposition Modeling" (FDM) (Iwan Zein et al, 2002). The filaments may be deposited according to any suitable orientation, for example the PLC filament layers may have an orientation of 0 degree, 60 degree and/or 120 degree (see FIG. 6A, B, C).

Design and Fabrication of PCL Scaffolds

Figure 6A:
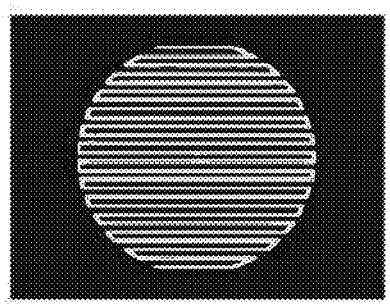
FIGS. 6A, 6B, and 6C show the 0/60/120° layer orientation of the PCL filament in the Burr Plug design. (a) 0 degree orientation of the PCL filament layer; (b) 60 degree orientation of the PCL filament layer; (c) 120 degree orientation of the PCL filament layer.
Figure 6B:
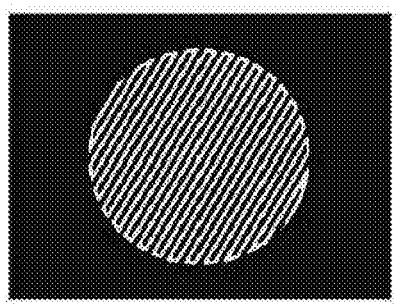
Figure 6C:
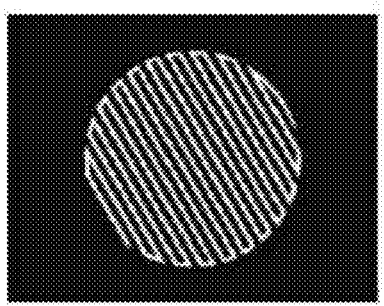

The biodegradable polymer implants are fabricated from a medical grade polycaprolactone (PCL, Viscosity 1.0-1.3; Birmingham, Al) using FDM rapid prototyping technology's (FDM 3D Modeller from Stratasys Inc., Eden Prairie, Minn.). The scaffolds have a completely interconnected porous architecture and a porosity of approximately 60 to 70%. The biodegradable polymer is TCP-PCL. In particular, three dimensional TCP-PCL (20:80%). More in particular, three dimensional TCP-PCL (20:80%) with 60-70% of porosity, preferably 65% of porosity. This morphology allowed cells to be trapped and proliferate when the scaffolds are implanted in the body (Hutmacher et al, 2001). The scaffold geometric models were first created in the Unigraphics CAD software and then exported into the Stratasys QuickSlice™ software in "STL file" format. For all the layers, a single contour and raster-fill pattern was adopted. A lay-down pattern of 0/60/120° were used to form the patterns of triangular pores (FIG. 6A,B,C). The method for producing the FDM filament is known in the art.

Cell may be cultured on the scaffolds. As an example, mesenchymal stem cell (MSC) may be used. Numerous studies have been undertaken to repair bone defects using MSCs seeded on porous scaffolds with either osteoconductive or osteoinductive properties. Caplan and Bruder (1997) were the first to describe a technique where large numbers of cells were cultured on to ceramic scaffolds prior to being surgically implanted into bone defects. However, to be useful clinically, problems with culture technique and scaffold properties must be overcome. Improved techniques to expand MSCs in culture to achieve more reliable mineralization and bone formation rates were the first to be developed. Subsequent, examinations using two-dimensional cultures of MSCs differentiated into osteoblasts have revealed a characteristic pattern of osteogenic development and established a hierarchy of events controlling the transition of MSCs into osteoblasts (Nicole et al, 2003). In addition to two-dimensional cultures, MSCs grown on various three-dimensional scaffolds have also been studied with initial seeding density having the greatest influence on ex vivo differentiation and subsequent in vivo bone formation. Furthermore, dense culturing of MSCs has been shown to enhance differentiation and mineralization, resulting in higher levels of alkaline phosphatase (AP) activity compared to low density cultures. To achieve a better osteoinductive environment, cell-sheets with high cell numbers have also been applied to three-dimensional scaffolds. This cell-sheet cluster technique has proven effective for tissue engineering in a number of contexts. Firstly, transplanting single cell-sheets for skin and cornea reconstruction has proven more successful compared with enzymatic treatments (Kushida et al., 2001). Secondly, layers of differing cell-sheets can be utilized for reconstructing complex tissues with multiple cell types. Using this technique, blood vessels have been engineered by culturing human cells, without synthetic or exogenous biological materials that demonstrate sufficient mechanical strength to warrant in vivo grafting (Nicolas, 1998). Lastly, by layering several types of cell-sheets, laminar structures can be fabricated including liver, kidney and vascular organs (Shimizu et al., 2001).

Further, the present invention also provides In particular, the plug implant is suitable to be inserted into a defect or a gap of a bone and the plug implant does not require means for fixing the plug to the external surface of the bone.

The plug implant may further comprise a bioactive agent.

The invention further provides a method for bone tissue regeneration comprising the steps of:

providing a bioabsorbable plug implant, wherein the implant comprises a first portion and a second portion extending outwardly from the first portion, the first and second portions formed from expandable material;

inserting the second portion into a defect or gap of a bone, the first surface engaging the outside contour of the defect or gap;

allowing the plug implant to contact body fluids, thereby expanding the size of the plug implant so that the plug fits into the defect or gap.

In the method of the invention, the implant may comprise a first and a second surface, opposite to each other, the first surface having an area smaller than the area of the second surface.

In the method of the invention, the plug implant may be formed from a porous material allowing the bone cells to penetrate into the plug implant and to regenerate the bone tissue. The plug implant may be shaped like a cone, truncated-cone, a pentahedron, a truncated-pentahedron, and/or a button mushroom. For instance, the first and second surface may have plane surfaces. Furthermore, the first and the second surfaces may have circular, square or rectangular shapes In the method of the invention, the plug implant may be formed from a porous material allowing the bone cells to penetrate into the plug implant and to regenerate the bone tissue.

The method of the invention can be used for bone tissue regeneration and bone reparation for any kind of bone structure, however, it is particularly suitable for performing cranioplasty.

According to the method, plug implant and the bone defect or gap have an initial tolerance of less than 1 mm. In particular, the initial tolerance is less than 0.5 mm. Preferably, the initial tolerance is less than 0.2 mm.

The method of the invention may also comprises placing catheter into an opening of the plug implant for performing drainage.

A characteristic of the method of the invention is that insertion of the plug implant into the bone defect does not require means for fixing the plug to the external surface of the bone surrounding the defect.

The method of the invention may be a therapeutic method for tissue bone regeneration and bone restoration of defects in animals, including humans. The method may also be a non therapeutic method for the cosmetic restoration of undesirable osseous gaps.

Having now generally described the invention, the same will be more readily understood through reference to the following examples which are provided by way of illustration, and are not intended to be limiting of the present invention.

EXAMPLES

Example 1

Pre-Clinical Trials Results

Figures 9A, 9B:
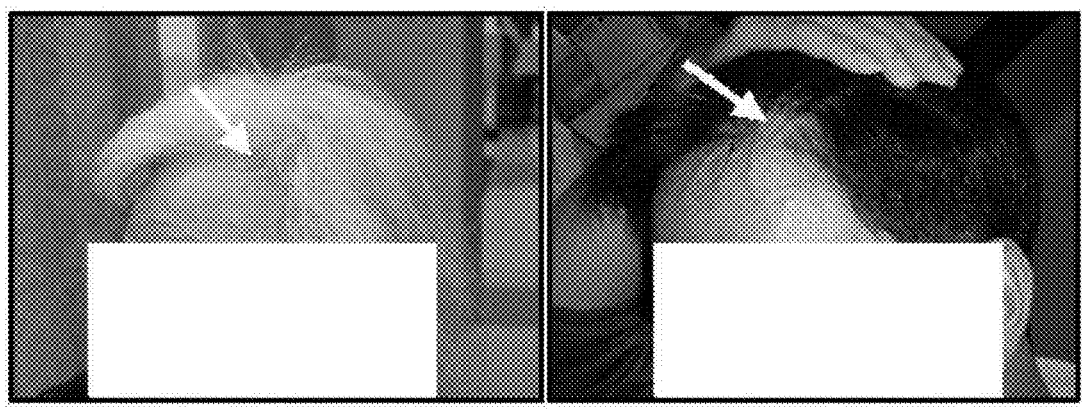
FIGS. 9A and 9B show postoperative views of two patients showing hair has grown on the skin covering the defect.

A pre-clinical study was conducted at the National University Hospital (NUH) on 10 patients. The study was reviewed by a National and International Ethics Advisory Board and approved by the Ethics Committee, NUH, Singapore. Patients eligible belong to those with chronic subdural hematoma. They were informed about different options prior to surgery. As an example FIG. 8, a (Left) shows a CT scan of two burr holes. A postoperative CT scan taken at day 3 revealed that the FDM PCL scaffold/cell graft was fixed in place and the 3D shape of the cranium had been well reconstructed. There were no mass effects or fluid collections present. The slow degradation kinetics of the PCL provides a stabile template and conforms to the shape of the skull. No swellings were present. As early as 3 month after implantation the implants were well integrated and started to mineralise (FIG. 8, b (Right)). Palpation reveals a stable integration of implant within the surrounding calvarial bone. Hair was observed to have also grown on the skin covering the defect (FIG. 9, a, b). The cosmetic effect is obvious and well accepted by the patients.

Example 2

In Vitro and in Vivo Use of Porcine Bone Mesenchymal Stem Cells Seeded into and Around Three-Dimensional TCP-PCL Scaffolds for Augmenting Bone Formation Bone tissue engineering has emerged as a promising technique for repairing bone defects. Using a combination of cell culture and a biodegradable scaffold, constructs with superior properties to conventional bone grafting may prove suitable for transplantation as a bone-graft substitute. In this study, we cultured autologous porcine mesenchymal stem cell (PMSCs) sheets on three-dimensional TCP-PCL scaffolds (20%) and examined their osteogenic differentiation as well as in vivo bone formation following transplantation under the skin of nude rats. Constructs consisting of 20% TCP-PCL with 65% porosity were used as three-dimensional matrices for PMSCs and cultured in vitro for up to 8 weeks. PMSC proliferation was assessed at regular intervals using a metabolic assay and confocal imaging. After 8 culture in osteoinductive media, PMSCs remained viable with mineralized nodules visible both inside and outside the scaffold. Intracellular alkaline phosphatase (ALP) activity increased >50 times following induction, with soluble ALP continuing to increase throughout the culture period. Similarly, mRNA expression for the osteogenic-related transcripts osterix, osteopontin (OPN), and osteocalcin (OCN), increased 4-10 times following induction, whilst core DNA binding factor 1 (Cbfa1) and collagen type I transcripts were slightly up regulated. At the protein level, OCN Increased 10 fold whilst OPN levels were elevated two to four fold. Following transplantation into nude rats, micro-CT and X-ray detected cortical as well as cancellous bone within in the constructs after 4 week that continued to increase with time. Most of the cortical bone was detected surrounding the construct, with cancellous bone within the construct. Histological examination revealed that bone formed within the constructs formed via endochondral ossification from the pool of seeded PMSCs. These findings demonstrate that PMSCs cell-sheet constructs proliferate and ossify both in vitro and in vivo and provide a useful three-dimensional model for examining of osteogenesis. Furthermore, the potential exists for using TCP-PCL constructs as a biodegradable scaffold ex vivo together with pre-seeded bone-cell sheets for transplantation into sites for clinical bone repair, especially for load bearing defects.

Materials and Methods:

Scaffold Fabrication and Characterization

Figure 11:
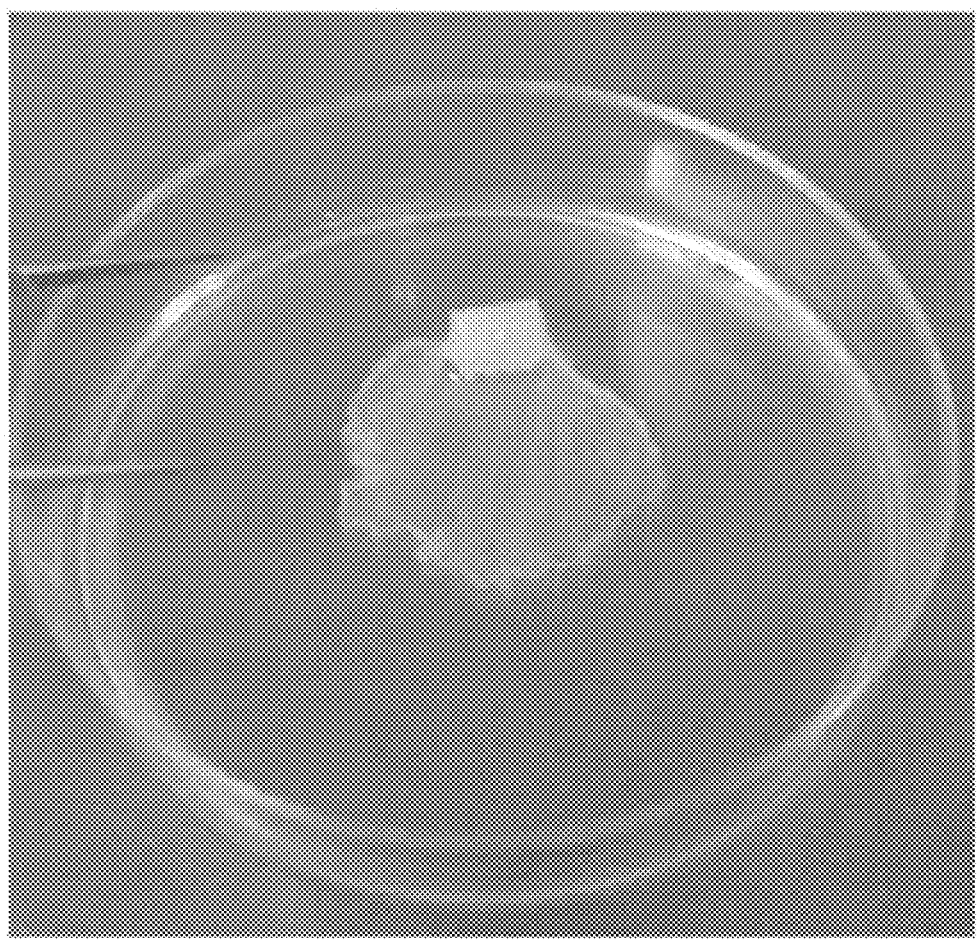
FIGS. 11 and 12 show the construction of sheet-scaffolds.
Figure 12:
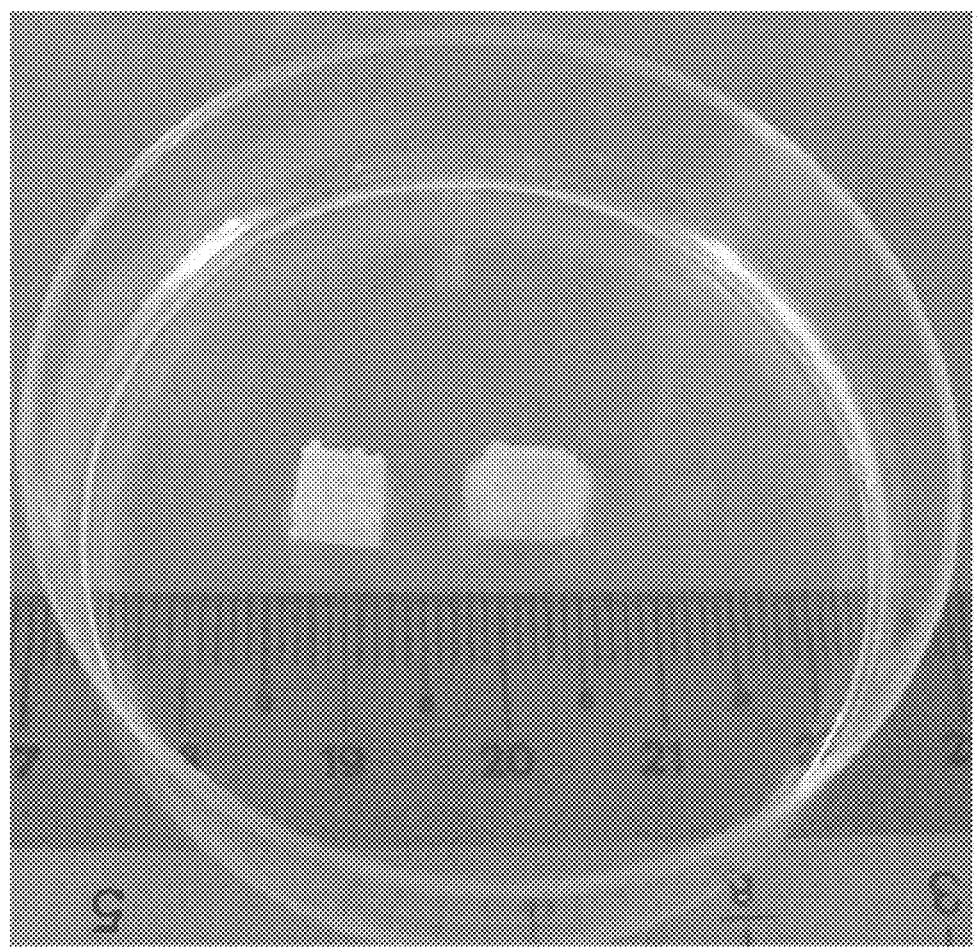

Until recently, the use of PCL (Sigma, USA) for scaffold fabrication has been restricted to non clinical applications. In order to adapt this technology for clinical applications we switched to medical grade PCL (Birmingham, Ala.) that has the same chemical composition and properties. Medical grade PCL/CaP flakes were prepared into Ø1.70±0.10 mm monofilaments via a filament extrusion process using an extruder built in-house prior to FDM fabrication (FIGS. 11 and 12). An FDM 3000 rapid prototyping system from Stratasys Inc was used to fabricate scaffolds with a bulk dimension of 40×40×4 mm (length, breadth and height, respectively). The working principle of the FDM has been described elsewhere (Caplan et al., 1997).

Scaffold porosity is defined as the ratio between true scaffold volume and apparent scaffold volume. The true volume is the volume of the material that makes up the scaffold, whereas, apparent volume is the scaffolds overall geometric volume, including air spaces within it. Scaffold porosity was measured as reported elsewhere, and the scaffold morphology and pore size were determined via scanning electron microscopy (SEM). Scaffold surfaces were gold-sputtered and examined using 15 kV accelerating voltage (Phillips XL30 FEG. Netherlands).

Compression testing was conducted with an Instron 4302 Material Testing System operated by Series IX Automated Materials Tester v. 7.43 system software with a 1-kN load-cell. Scaffolds were examined in accordance with the ASTM D695-96 guidelines. The specimens were compressed at a rate of 1 mm/min up to a strain level of approximately 0.6 N. The stress-strain ($\sigma$–$\epsilon$) curve was calculated and the compressive stiffness (Young's modulus) and compressive yield strengths of the scaffolds determined. Stiffness was then calculated from the stress-strain curve by defining the slope of the initial linear portion of the curve, with any toe region (the initial settling of the specimen) neglected. The compressive yield strength was taken at the yield point (if any) or at the end of the linear region.

Thermal analyses, utilizing differential scanning calorimetry (DSC), were conducted to study the thermal response of the materials and to determine the fractional crystallinity of the polymer. The heat-flux Pyris 6 DSC from Perkin-Elmer was used with the average sample weight of 5-12 mg held in standard aluminum pans and covers, from Perkin-Elmer. The specimens were scanned from 20 to 80° C. at a ramp rate of 5° C./min, using nitrogen as purge gas. Crystallinity fractions were calculated based on an enthalpy of fusion value of 139.5 J/g for 100% crystalline PCL [Pitt et al., 1981].

The average molecular weight of the PCL was determined by high performance liquid chromatography utilizing a gel permeation chromatography (GPC) apparatus. Sections of the PCL scaffolds were cut and dissolved in tetrahydrofuran (THF) at a concentration of ≤0.1% (≤1 mg/ml). The sample solution was further filtered through a 0.2 μm inorganic membrane filter and the polymer molecular weight distribution determined using a GPC equipped with a differential refractor (Waters 410) and an absorbance detector refractor (Waters 2690). The samples were eluted through a Styragel column refractor at a flow rate of 1 ml/min, using THF as the mobile phase. Polystyrene standards (Polysciences) were used to obtain a calibration curve. Both the weight average molecular weight ($M_w$) and number average molecular weight ($M_n$) were evaluated, along with the polydispersity ($M_w/M_n$).

Where appropriate, statistical analysis was performed using the Student's t-test set at a confidence level of 95% ($p<0.05$).

Cell Isolation and Culture

Porcine mescenchymal stem cells were isolated and cultured as reported previously (Hutmacher, et al., 2001). Pigs were obtained from the Animal Holding Unit of the National University of Singapore (NUS) after appropriate ethical clearance was granted and samples of bone marrow removed according to the NUS animal ethics guidelines. Briefly, MSCs were aspirated from the bone marrow and gradient centrifugated, prior to being cultured in Dulbecco's Modified Eagle's medium (DMEM) low glucose (GIBCO, Invitrogen, CA, USA) containing 2% fungizone (Sigma, Mo., USA) and 2% antibiotics (200 μg/ml penicillium and 200 μg/ml streptomycin), herein referred to as standard media, at 37° C. and 5% CO2 in a humidified environment. Cells were initially seeded at a density of $2\times10^5$ cells per 75 square centimeter flask. Only passage two to four cultures were used for all the experiments. At confluence, culture media was changed to osteogenic media consisting of standard media plus L-ascorbic acid-2-phosphate (50 ug/ml), β-glycerophophate (10 mM) and dexamethasone (100 nM) (Sigma, USA) to induce osteogenic differentiation (induced). Control cultures (non-induced) were maintained in standard media. All media was changed every two days.

Scaffold Fabrication and Cell Seeding

Figure 10:
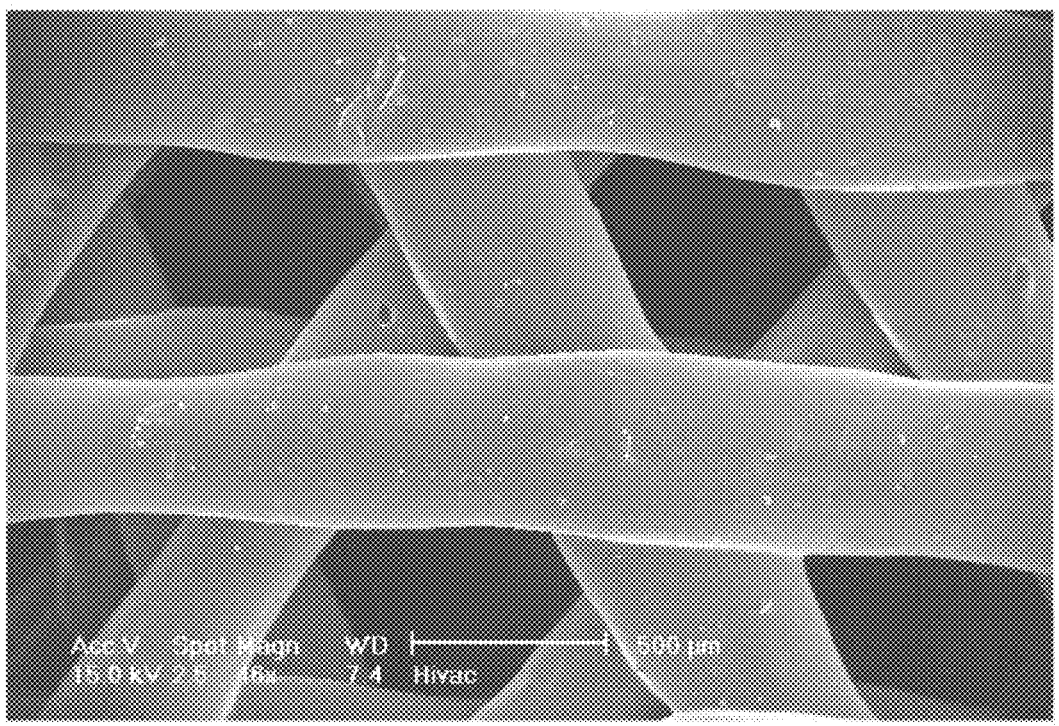
FIG. 10 show the structure of a 20% TPC PCL scaffold. SEM of empty TPC-PCL scaffolds revealed interconnecting pores of 400-600 µm in diameter.

TCP-PCL (20:80%) scaffolds, each with a lay down pattern of 0/60/120 and a porosity of 65%, were fabricated by fused deposition modeling (FDM) according to our previous methods (Hutmacher et al 2001) (FIGS. 10, 11 and 12). TCP-PCL scaffolds were cut into 4 mm×5 mm×5 mm blocks and treated with 5M NaOH for 1 h to improve the hydrophobic property of the scaffold surface. Scaffolds were then thoroughly rinsed with PBS to wash away NaOH residues and soaked in 75% EtOH for at least half an hour and allowed to air dry. Cells ($5\times10^5$ in 20 μl) in standard media were then seeded into the scaffolds and allowed to adhere for 2 h at 37° C. before additional media was added.

Cell Sheet-Scaffold Construction

Confluent induced (Group A) and non-induced (Group B) MSCs sheets (25 cm$^2$) were gently peeled from the flasks using sterile fine forceps and wrapped over the pre-seeded scaffolds and cultured for one week. These constructs were then divided into three groups a) induced cell sheet-scaffolds construct; b) un-induced construct; maintained for up to 8 weeks: c) 2D plates. For the in vivo implantation, the scaffold size was 10 mm×10 mm×4 mm and seeded inside with 1 million MSCs then wrapped with cell sheet form 75 square centimeter flask. All the cells used in implantation were cultured in vitro for 4 weeks. Implantation was classified into two groups: a) induced; b) un-induced sheet-scaffolds constructs. The induced constructs were confirmed to have undergone ostegenic process and mineralization before implantation.

Cell Viability and Phalloidin Staining

Cell viability was assessed by a live-dead assay using a combination of fluorescein diacetate (FDA) and propidium iodide (PI) (Molecular Probes Inc., Oregon, USA). Fluoresent photomicrographs were taken of each group using confocal laser microscopy (CLM) (Leica, Germany). Prior to FDA/PI treatment, constructs were removed from the culture wells, rinsed in PBS and Incubated at 37° C. with 2 µg/ml FDA in PBS for 15 min. After washing with non-sterile PBS, specimens were then placed in 0.1 mg/ml propidium iodide solution in PBS for 2 min at room temperature. The specimens were then washed again in PBS, placed on a microscopical cover glass, and viewed by confocal microscopy.

Cell Labeling and Alamar Blue Assay

MSCs were labeled with cFDA (Molecular Probes) then washed with PBS and labeled with green fluorescence at 37° C. for 15 min according the manufacturer's instructions, prior to implantation.

To determine growth, 1 ml of alamar blue (Probes, Oreg., USA) (10% (v/v) was added to cultures containing cell/scaffold constructs at various timepoints and incubated for 3 h. Assay media was then transferred to a 96-well plate and the absorbance at 570 nm and 600 nm were determined with a microplate reader (Brand, Calif., USA). Reduction rate was calculated according to the products instruction.

Alkaline Phosphatase Activity

Cellular alkaline phosphatase (AP) activity was determined using a kinetic assay based on measuring the rate of p-nitrophenol formation from p-nitrophenyl phosphate (procedure no. 104, Sigma). Briefly, cell lysates were prepared by removing the media and adding ice-cold buffer (5 mM $MgCl_2$, 150 mM NaCl, 1% triton-100, pH 7.5) containing a protease inhibitor cocktail (Calbiochem, UK). Protein supernatant was then collected by centrifugation at 12,000×g for 5 min and the protein content determined using a Protein Assay Kit (Cat No. 500-0002, Bio-Rad). Samples (20 µl) were combined with 50 µl of AP reagent and the activity measured in a 96-well plate following an incubation of 30 min at 37° C. AP activity was read at 405 nm (Bio-Rad microplate reader benchmark 10892, Bio-Rad, USA) as per the manufactures instructions and the amount of enzyme determined by comparison with a standard curve. AP activity in the lysates was expressed as nanomoles of p-nitrophenol produced per minute per microgram of protein.

RNA Isolation and RT-PCR

Total cellular RNA was extracted weekly using Trizol reagent (Invitrogen Corp., Carlsbad, Calif., USA according to the manufacturer's recommendations. cDNA synthesis was performed from 2 µg total RNA using Superscript II and Oligo dT (Invitrogen Corp., Carlsbad, Calif., USA) according to the manufacturer's instructions. The expression of cbfa-1, osterix, collagen I, osteopontin and osteocalcin was quantitated by real-time PCR using an ABI Prism 7000 Sequence Detector and SYBR Green PCR Master Mix (Applied Biosystems, Foster City, Calif., USA) using specific primers synthesized by Proligo (Singapore). Primer sequences were designed with the Primer Express® program v 2.0 from Applied Biosystems and were blasted for their specificity at the National Centre for Biotechnology Information (NCBI). Measuring the increase in fluorescence caused by the binding of SYBR Green to double-stranded DNA directly during PCR cycles monitored the increase in reaction products during PCR. Reaction mixtures were setup following the manufacturer's instructions. Following a 8 min Taq Polymerase activation step at 95° C., the reactions were cycled by denaturing for 30 sec at 95° C. and annealing and elongation for 1 min at 60° C. (same for each primer) and extension at 72° C. for 1 min and repeated for 35 cycles, before a final extension period of 72° C. for 7 min. Target gene $C_T$ values were expressed as Relative Expression Units (REU) and standardized against GAPDH. The reaction products were also cloned into pGEM-TEasy vector (Promega) and sequenced for confirmation.

Western Blot

Cell lysates were prepared by using ice-cold lysis buffer (1% Triton X100, 150 mM NaCl, 10 mM Tris pH 7.4, 2 mM EDTA, 0.5% NP 40, 0.1% SDS) containing protease inhibitors (1 mM sodium orthovanadate, 10 ug/mL leupeptin, 1 ug/mL aprotinin and 1 mM PMSF). The protein concentrations in the supernatant were determined using a Protein Assay Kit (Bio-Rad) according to the manufacturer's recommendations. Cell lysates (40 ug) were resolved by 6-12% SDS-PAGE (polyacrylamide gel electrophoresis) gels and the proteins were transferred to nitrocellulose membranes (Amersham, Buckinhamshire, UK). Non-specific binding was blocked with 5% low fat milk in tris-buffered saline (TBS) for 1 h at room temperature (RT). Membranes were then washed twice with TBS and incubated with either mouse anti-OCN (Biodesign, ME, USA), -OPN (DSHB, IA, USA) or -actin (Santa Cruz, Calif., USA primary antibody diluted 1:1000 in TBS with 0.1% Tween (TBST) overnight at 4° C., washed, then incubated for 1 h with secondary antibody diluted 1:1000 in TBST, washed, and developed by chemiluminescence (Supersignal west pico kit, Pierce, USA). OPN antibodies were obtained from the Developmental Studies Hybridoma Bank developed under the auspices of the NICHD and maintained by the University of Iowa, Department of Biological Sciences, Iowa City, Iowa 52242

Von Kossa Histochemistry and Scanning Electron Microscopy (SEM)

von Kossa histochemistry was utilized to assess the degree of mineralization throughout the scaffold-cell construct. Briefly, constructs were washed in PBS and fixed with 4% paraformaldehyde (Sigma) and washed with ultra pure water (UPW). Sections (25 µm thick) were treated with 1% $AgNO_3$ (Sigma) for 45 mins under ultraviolet radiation and washed UPW. Sections were then treated with 5% (w/v) sodium carbonate solution for 8 minutes; rewashed with UPW and treated with 5% (w/v) sodium thiosulfate (Sigma) and bone nodules photographed using a dissection microscope (Zeiss, Jena, Germany) equipped with a digital camera (AxioCam; Zeiss) using AxioVision Software version 3.1 (Zeiss).

For SEM analysis, cells in the scaffold-constructs were fixed in 3% gluteraldehyde in a cacodylate buffer. Fixed cells were then incubated in 1% $OsO_4$ (ProSciTech) and dehydrated using ethanol. Constructs were then embedded in Hexamethyldisilazane (HMDS) (ProSciTech) and platinum coated with a sputter coater (Eiko, Japan). Samples were then examined by XL30SEM (FEI Inc, OR, USA) at 15 Kv.

Histology

Specimens for routine histological analyses were fixed in 3.7% formalin (Sigma), embedded in tissue-tek (Germany) and sectioned with a Cryomicrotome (Leica). Section 7 µm thick were mounted on poly-L-lysine (Sigma) pre-coated slides. Sections were then stained with hemotoxylin and eosin and neutral red (Hutmacher, 2003).

MicroCT Scan and X-Ray Analysis

A Skyscan in vivo microtomograph 1076 µCT scanner was used to determine bone growth occurring in the cells/scaffolds constructs. Specimens were placed on 68 mm wide sample holders and the constructs placed with the height and width parallel to the scanning plane. A scanning resolution of 35 μm, with an averaging of 5 was used together with a 1 mm aluminum filter and a rotation step of 0.8° and a rotation angle of 180°. Approximately 500 scan slices were taken and the files reconstructed at a step size of 4 using a modified Feldkamp algorithm according to the manufactures recommendations (Skyscan). The output was a series of 120 serial 1968×1968 bitmap images which were later reconstructed into 3D stacks using Mimics 7.3, Mimics enabled the volume and surface area of the bone growth to be calculated. In addition to volume and surface area measurements, the degree of new bone growth within the cell/scaffold construct was also assessed based on thresholding standards. These standards (cancellous and cortical bone) were calculated from newly harvested samples of procine bone using the profiling function of Mimics. The calculated thresholds used in this study were 68 to 1732 HU (Housefield units) for cortical bone and −70 to 67 HU for cancellous bone.

As convention x-ray analysis, sample were analysed using a Mammomat 3000 (Siemens) X-ray machine. The voltage and current employed during the imaging was adjusted in order to achieve the best clarity and resolution.

Ectopic Implantation

The animal research protocol was reviewed and approved by the Animal ethics committee, National University of Singapore (NUS) (small animal protocol NIDCR 00-113). Nude rats, mu/mu, originally obtained from Harlan Sprague Dawley (Indianapolis, Ind.) were bred and maintained at the NUS Animal Facility (Buffalo, N.Y.) in specific pathogen-free conditions. All animal procedures were performed in a laminar flow hood. Cell/Scaffold constructs (2 Induced and 2 non-induced constructs per animal) were transplanted subcutaneously into the dorsal surface of three to four month-old immunocompromised rats weighing between 110 and 130 g. Transplants were recovered 4, 8 and 12-weeks post-transplantation, fixed in 4% formalin, and either decalcified in 10% EDTA (pH 8.0) for paraffin embedding or fixed in 70% ethanol and resin embedded in Technovit 8100 embedded in resin (Technovit 8100, Kulzer, Germany) according to the manufactures recommendations. Paraffin sections (10 μm) were deparaffinized, hydrated, and stained with hematoxylin and eosin (H&E). Plastic sections were processed with H&E and von Kossa staining. For quantitation of new bone formation in vivo, NIH Image was used to calculate five representative areas at 5× magnification from either induced or 2 non-induced transplants.

Statistics Analysis

All values were presented as mean±standard deviations. All data was subjected to two-way ANOVA and Bonferroni post-hoc testing and pairwise comparison (SPSS Version 11.02). Significance levels were set a p<0.05. Data were the average of 3 replicates performed under identical conditions.

Results

MSCs Grow on Scaffolds

Figure 13:
FIG. 13. Cell attachment (phalloidin stain) (200×) of an in vitro culture at 3 weeks.
Figure 14A:
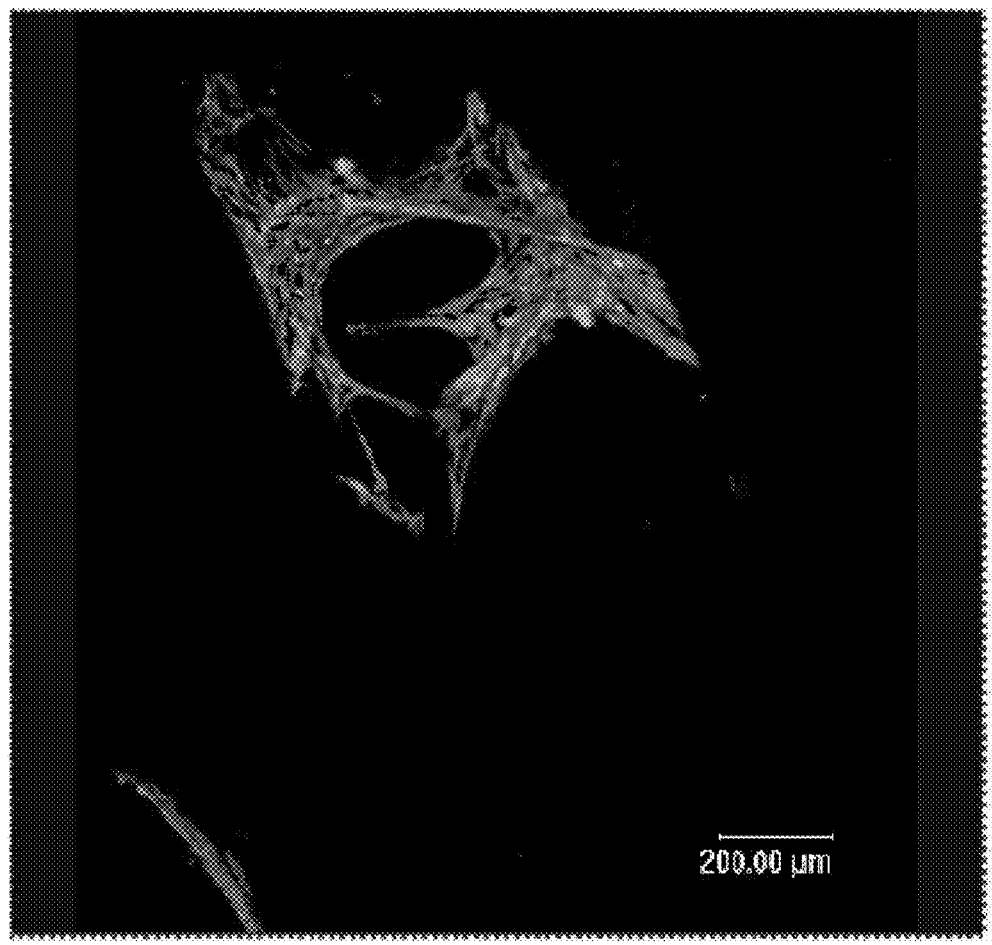
FIGS. 14A and 14B show proliferation (FDA-PI stain inside) with FIG. 14A showing in vitro 1 week (100×) and FIG. 14B showing in vitro 5 weeks (200×).
Figure 14B:
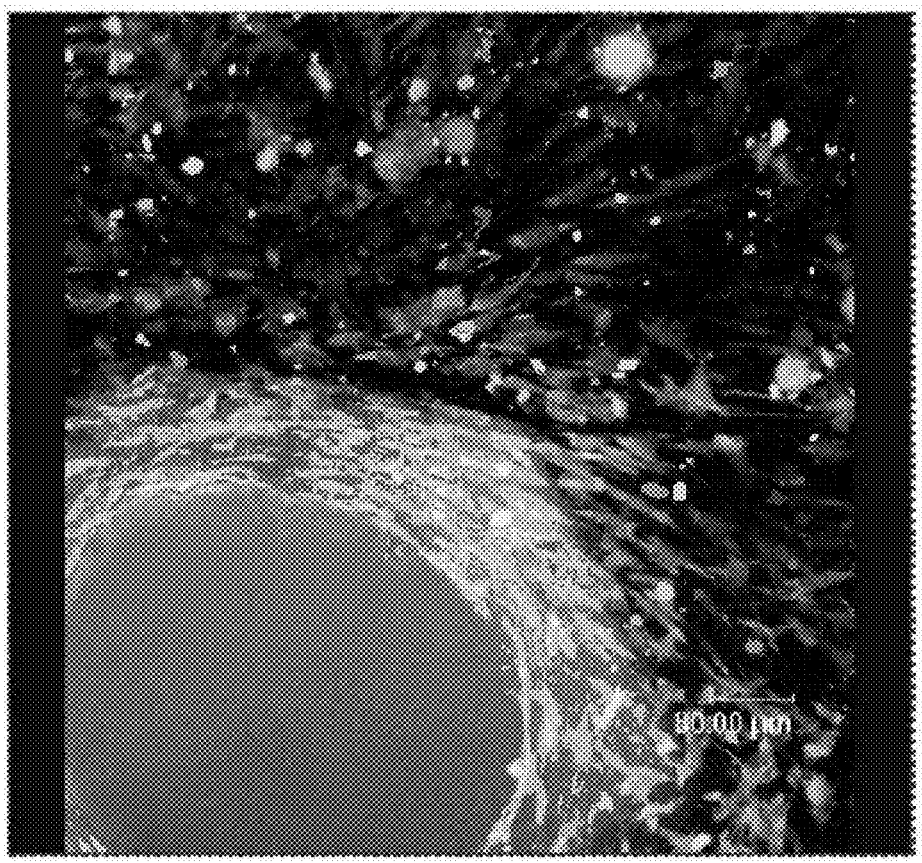
Figure 15A:
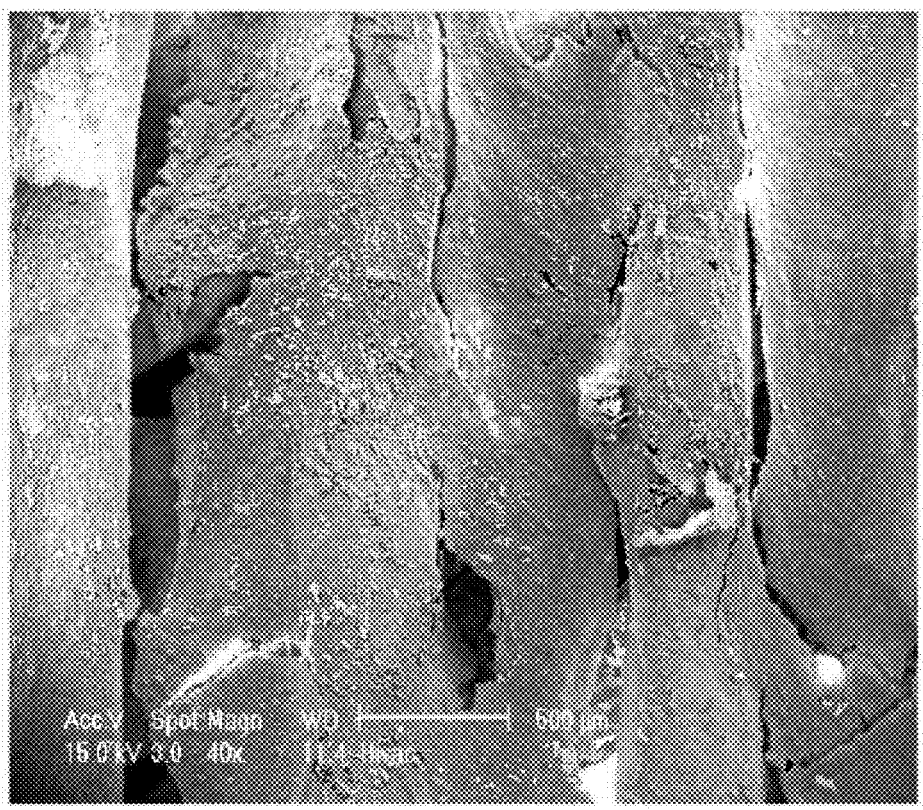
FIGS. 15A and 15B depict cell sheet-scaffold constructs. The photos in FIG. 15A depict a top view
Figure 15B:
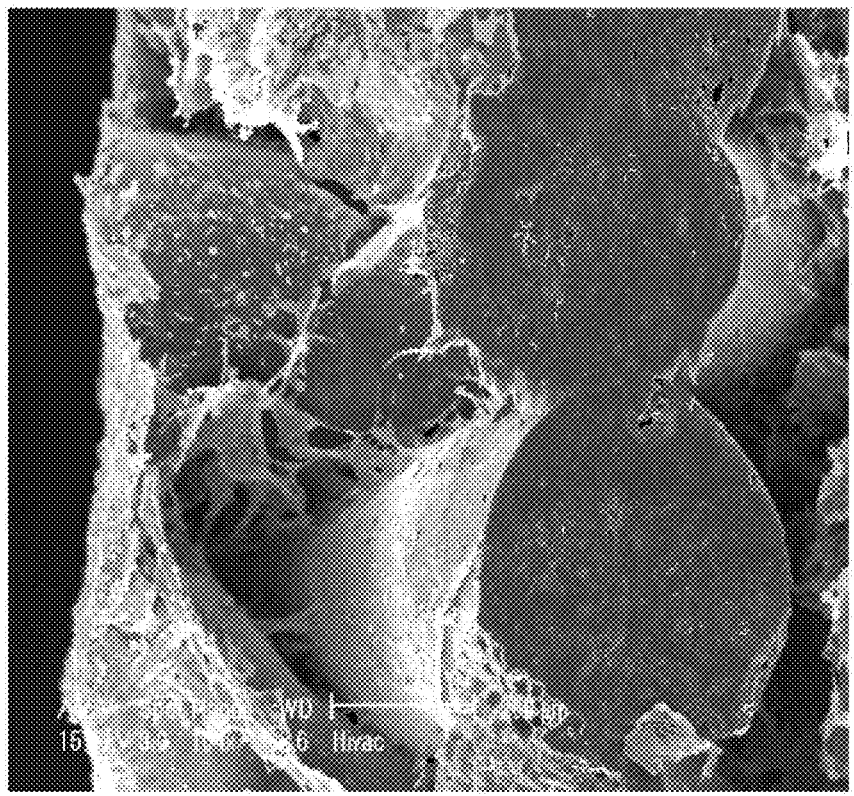
Figure 16A:
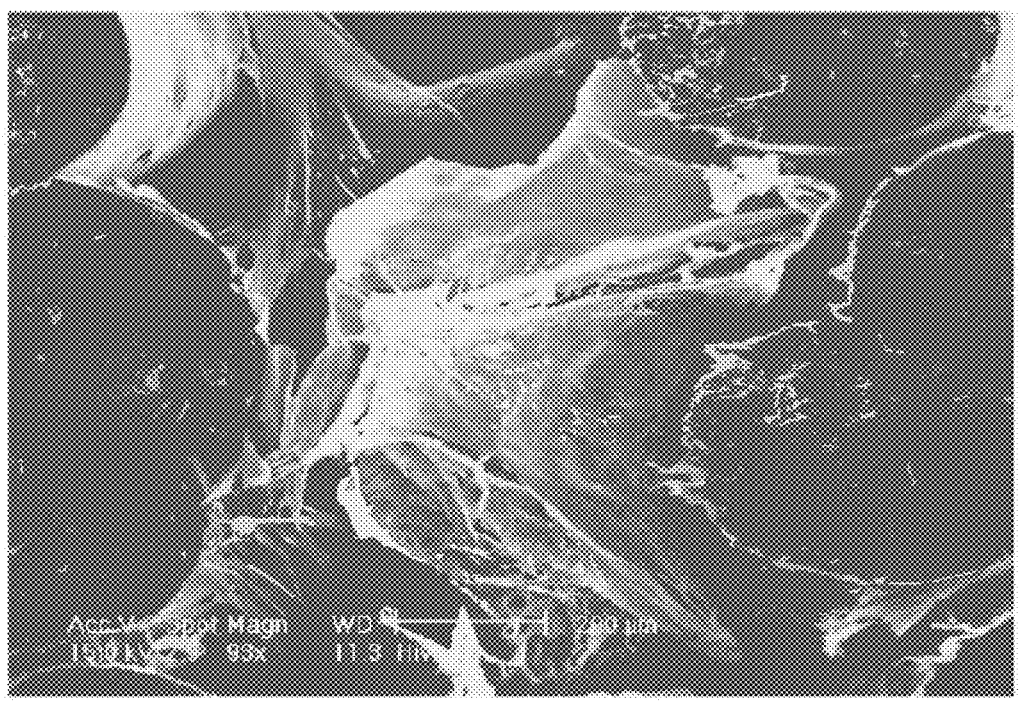
FIGS. 16A and 16B depict cell sheet-scaffold constructs (Inside scaffolds) with FIG. 16A showing the side view, and FIG. 16B showing the top view.
Figure 16B:
Figure 17A:
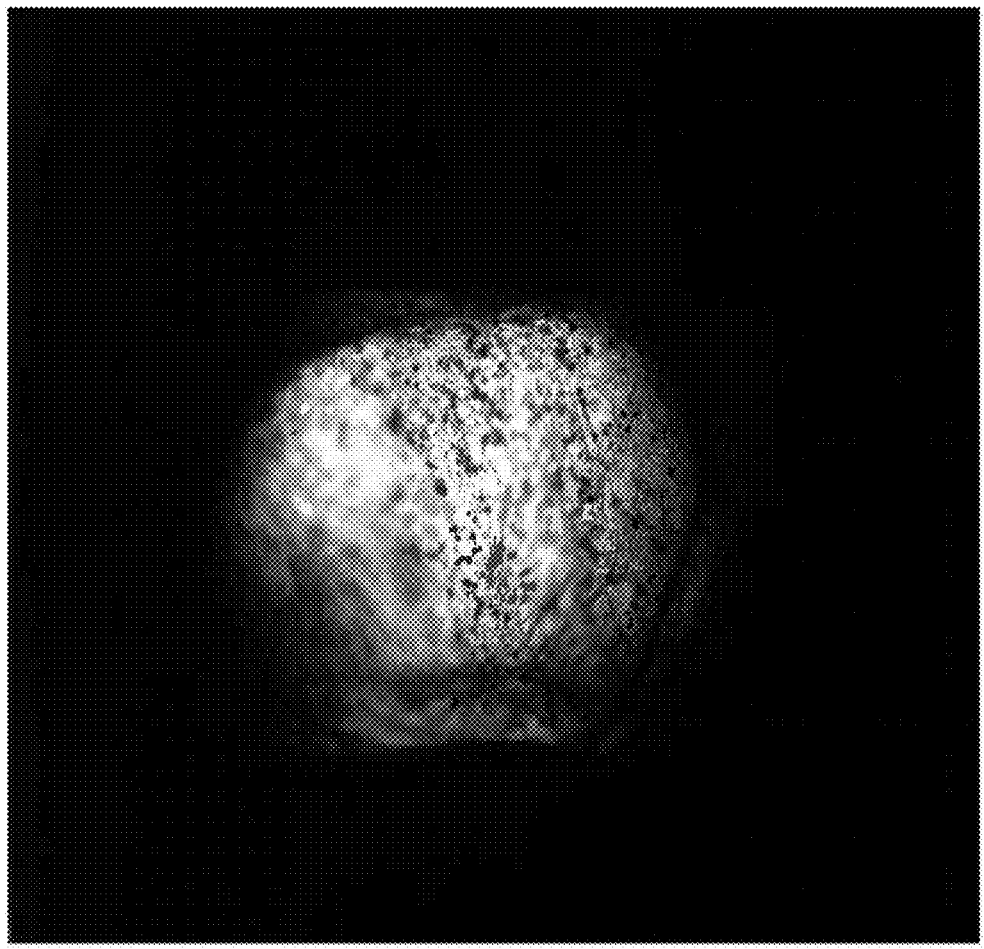
FIGS. 17A and 17B depict von Kossa stain on constructs with FIG. 17A (100×) and FIG. 17B (400×) showing mineral nodules formed in the scaffolds, 5 weeks after induction.
Figure 17B:
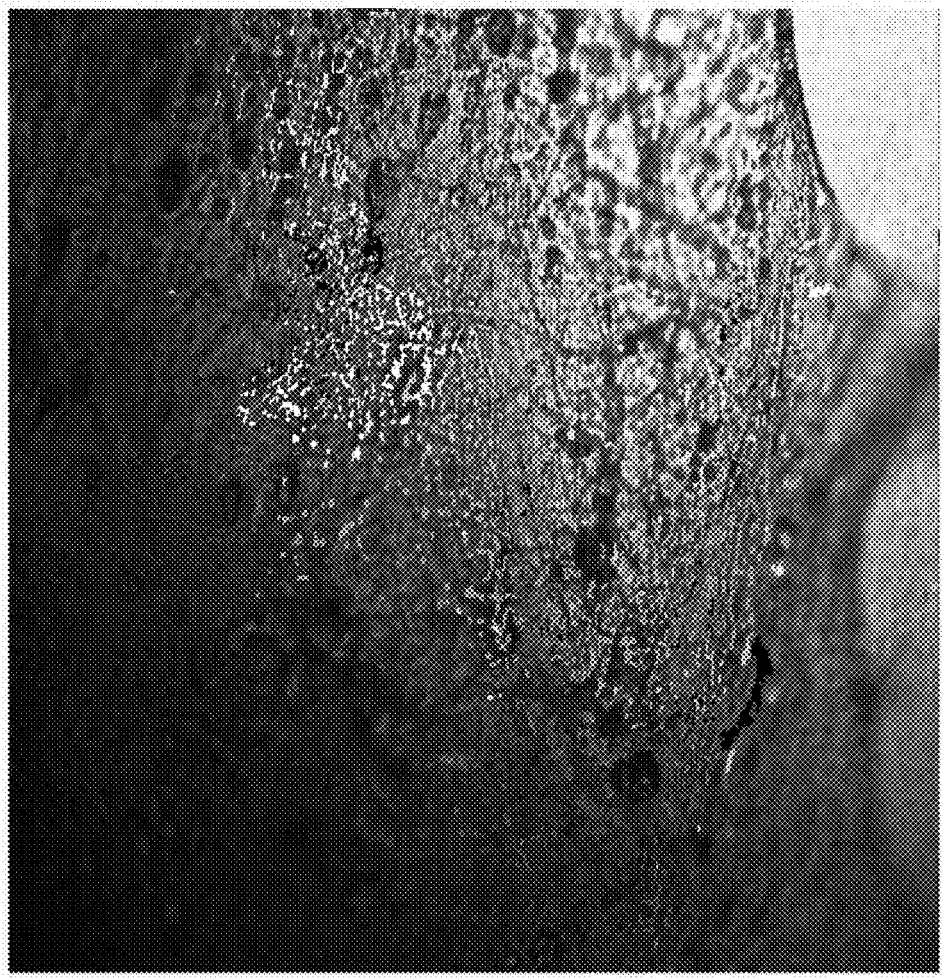

Adhesion and viability of MSCs seeded and wrapped on scaffolds were evaluated at various time points. After 3 days of culture. MSCs attached on the bars of scaffolds and the pholloind staining visualized the actin fiber formed by MSCs and accumulated on the contact point of cell-scaffold. After three weeks, the bar of scaffolds was fully covered by MSCs and cells evenly spread on the surface of scaffolds (FIG. 13). For the cells inside scaffolds after 1 week, MSCs formed bridges over the pores of scaffolds via the production of ECM (FIG. 14A). Hence forth, after 5 weeks, Most of pores were filled with cells and ECM and only few dead cells were observed (FIG. 14B). Cell sheet wrapped on the scaffold formed ECMs and stained viable up to 8 weeks. FIG. 15A,B of SEM images revealed that the collagen fibers formed by MSCs. The sheet formed on the surface of scaffolds and cell layers formed within constructs after osteogenic induction (FIG. 16A,B). Mineral nodules formed in induced constructs were firstly detected in 3 weeks by von Kossa staining (FIG. 17A,B).

Figure 18:
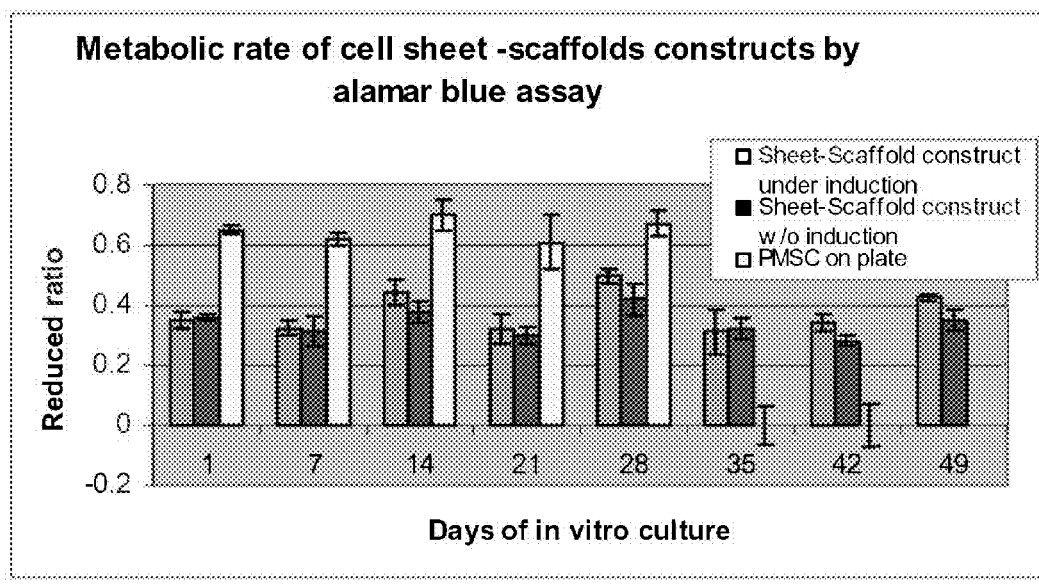
FIG. 18. Alamar blue assay.

The metabolic rate of constructs at different point was measured using alamar blue dye conversion ratio as shown in FIG. 18. The reduced ratio of constructs under osteogenic induction was slightly higher than that of constructs without induction. The reduced ratio of constructs increased at week 2 and remained stable up to 7 weeks. For the cells cultured on plate, the ratio was higher than cell sheet-scaffolds constructs. However, it is difficult to compare since the two culture system had different substratum and seeding density.

ALPase Activity

Figure 19:
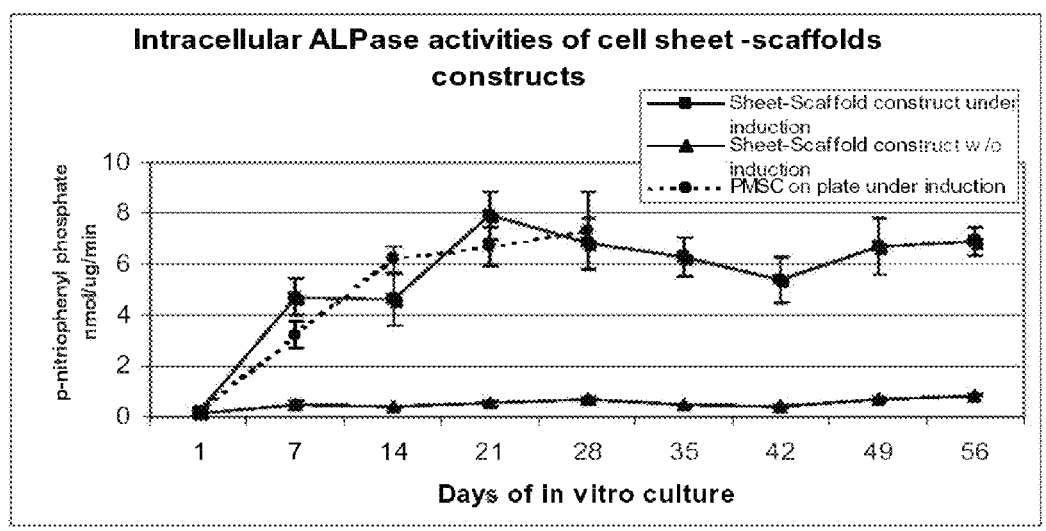
FIG. 19. Intracellular ALPase activities of cell sheet-scaffolds constructs.
Figure 20:
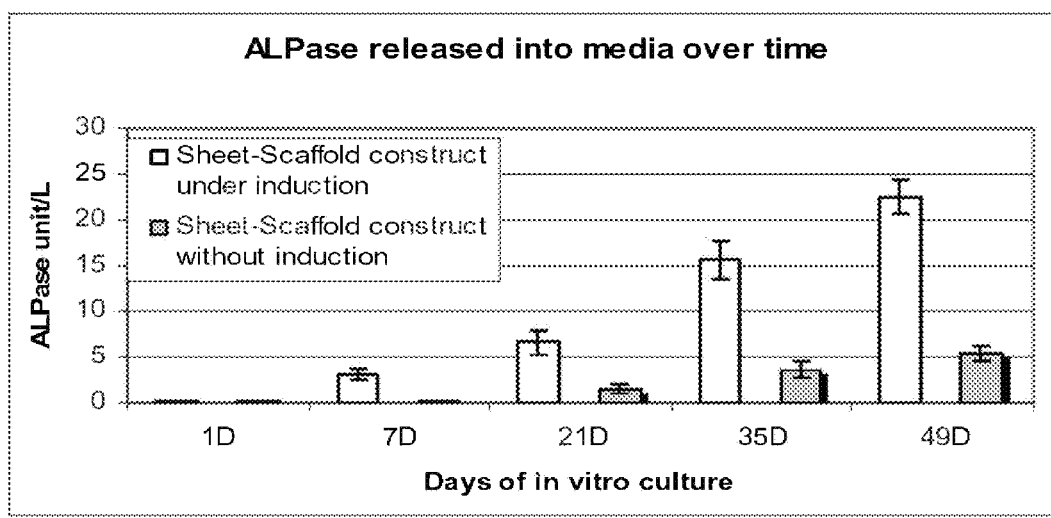
FIG. 20. ALPase released in media by ELISA.

To quantify the osteogenic ability of constructs in vitro, extracellular and intracellular ALPase activities were monitored. FIG. 19 shows the ALP released into media increased with the time of culture after induction. At 49 days, the ALPase activity of induced constructs was 10 times over the un-induced. For the intracellular ALPase, its activity was sharply increased over 30 folds at week 1 and peaked at week 3 (FIG. 20). Its level remained over the whole culture period up to week 8.

Expression of Osteo-Related Biomarkers

Figure 21:
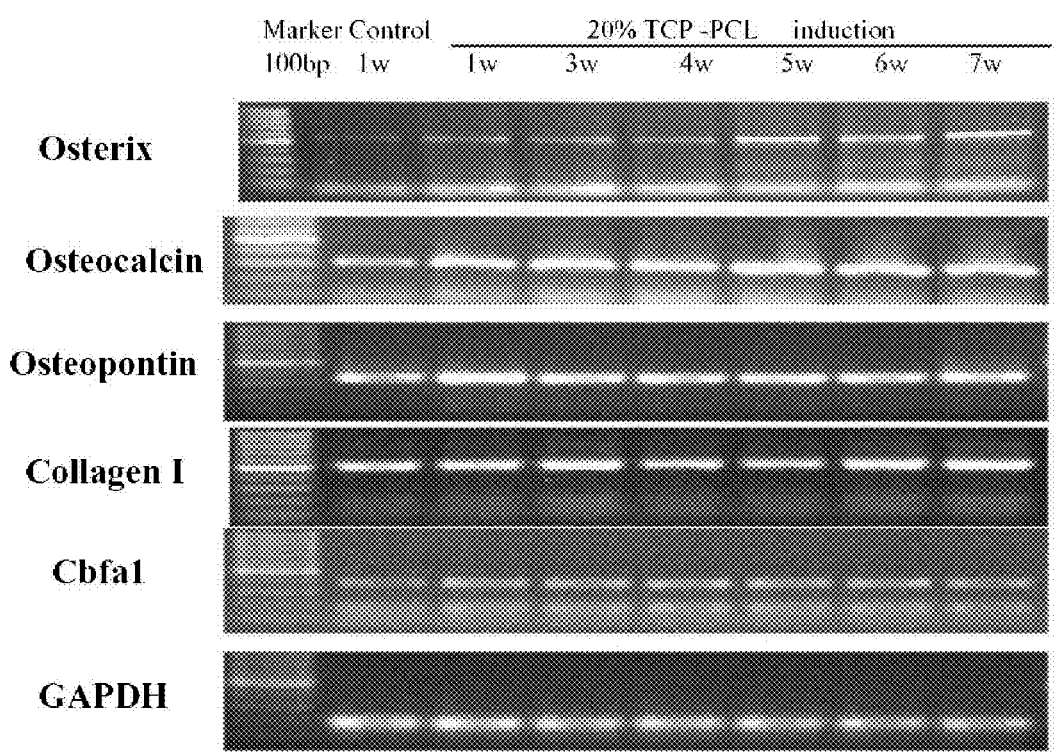
FIG. 21. RT-PCR Assay. In vitro RT-PCR profiles show osterix, osteocalcin and osteopontin mRNA expression level of sheet-scaffolds constructs significantly increased after induction, while collagen type I and Cbfa1 expression level are slightly increased.
Figure 22:
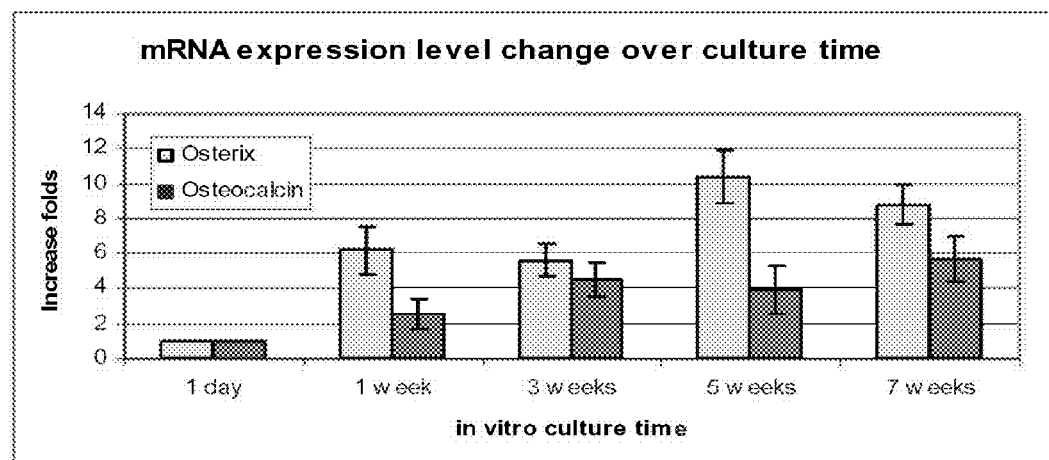
FIG. 22. RT-PCR assay on expression level of osterix and osteocalcin. The expression level of osterix and osteocalcin are up-regulated to 10 to 5 times after osteogenic induction. Data were calculated according to the density of PCR products.
Figure 23:
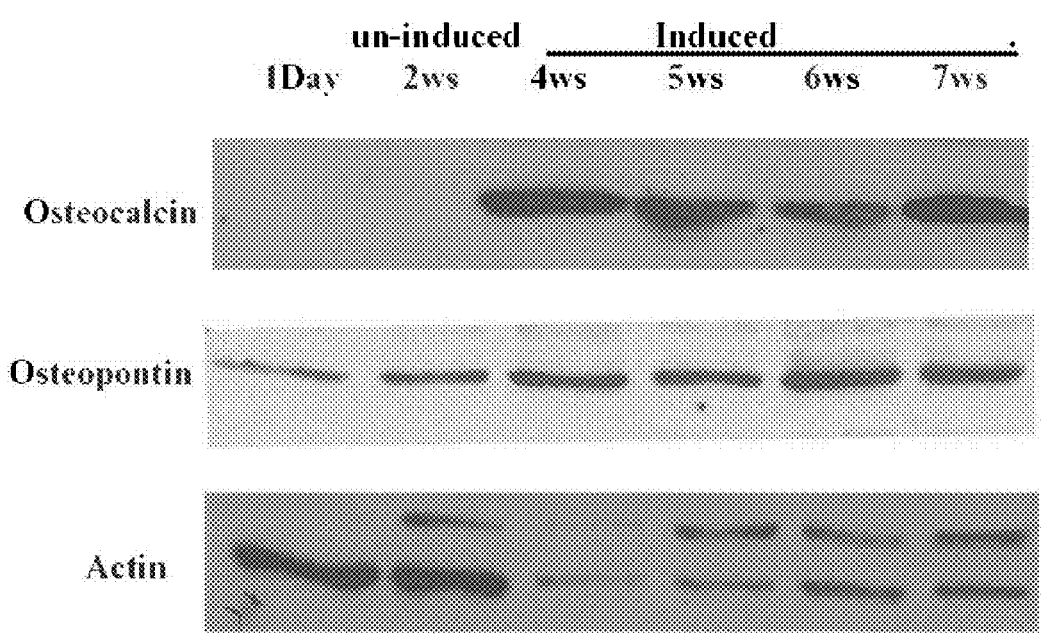
FIGS. 23 and 24. Protein profiles show that osteocalcin in sheet-scaffolds constructs is specifically observed after osteogenic induction, and osteopontin expression level is sharply up-regulated 4-5 times after induction.
Figure 24:
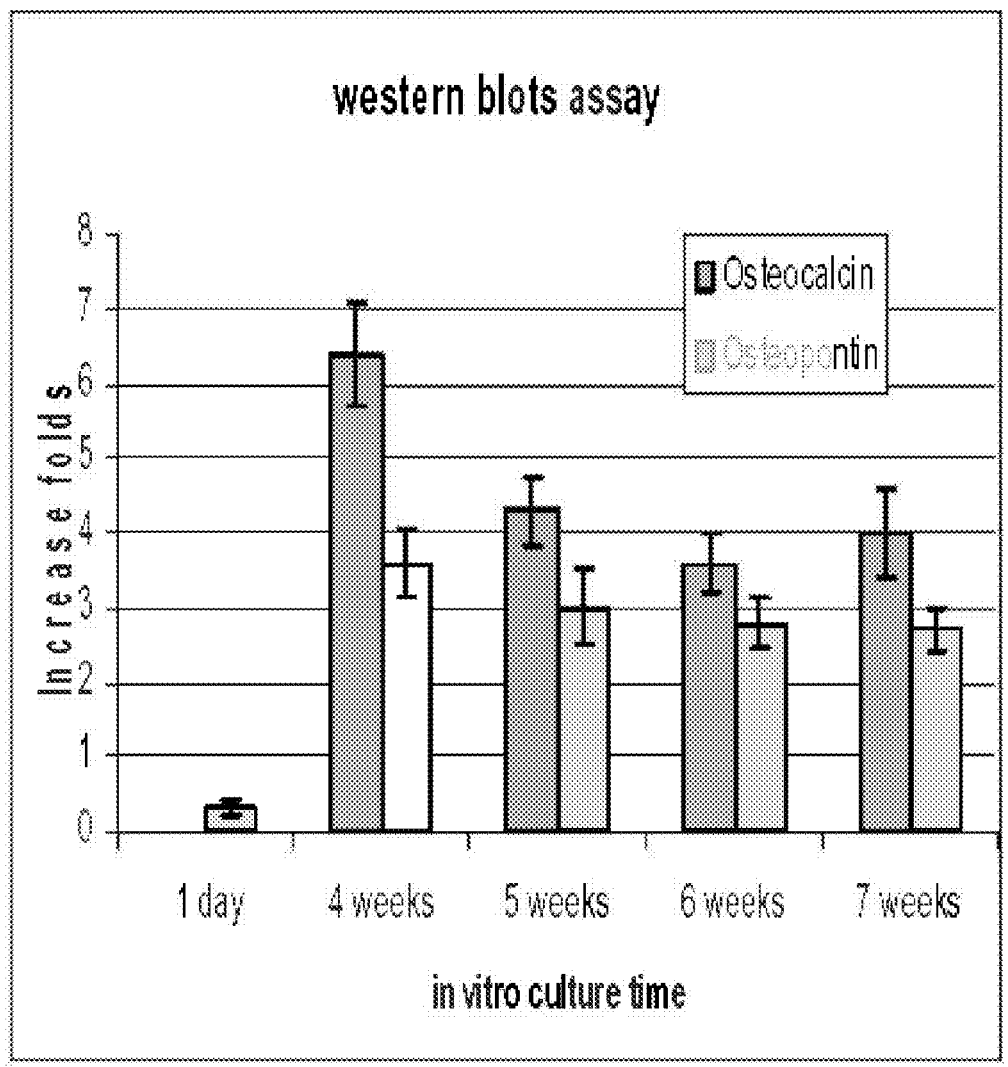

To confirm the osteogenic differentiation process of the construct in vitro, the RNA of constructs were extracted and RT-PCR was applied to monitor the temporal expression levels of osteo-related molecules, namely two important transcription factors, Cbfa1 and osterix, osteocalcin (OCN), osteopontin (OPN) and collagen type I (Col I) (FIG. 21). FIG. 22 shows that osterix and ocn expression level were significantly up-regulated at least 10 and 5 times respectively after induction and kept the high level over the culture period. OPN expression level was up regulated as well and the levels of cbfa1 and Col I were slightly increased in induced constructs. To further confirm certain key molecules in osteogenesis, OCN and OPN protein synthesis were also measured through western blots (FIG. 23, 24). As shown in FIG. 24, OCN was specifically expressed at induced constructs and its expression remained stable over 7 weeks culture, OPN expression increased around 3-4 times at week 3 and then slightly decreased.

Bone Formation In Vivo

Figure 25A:
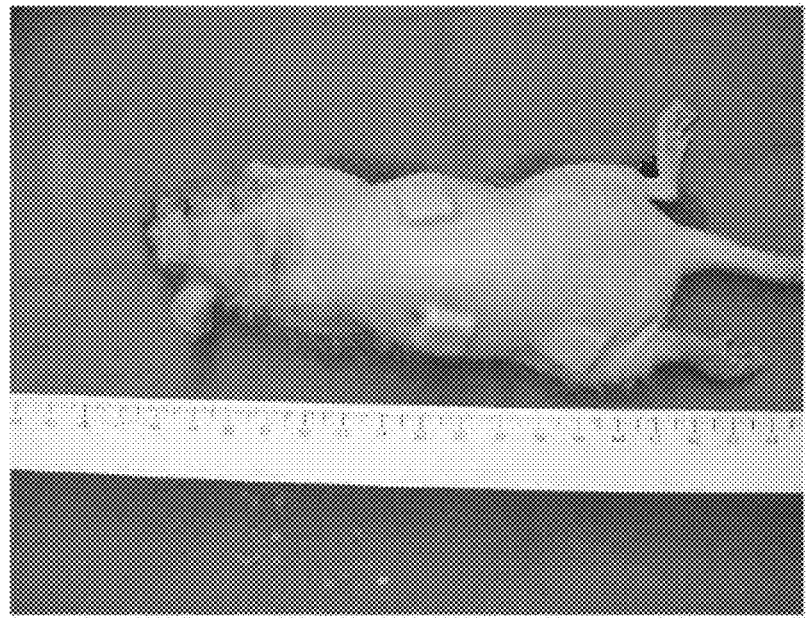
FIGS. 25A and 25B depict implantation of sheet-scaffolds constructs.
Figure 25B:
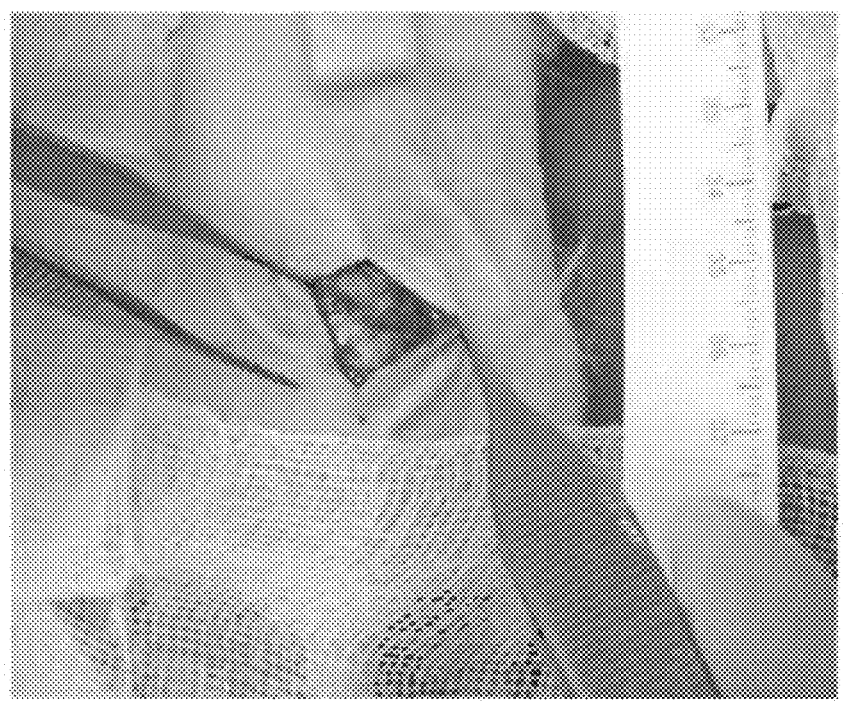
Figure 26A:
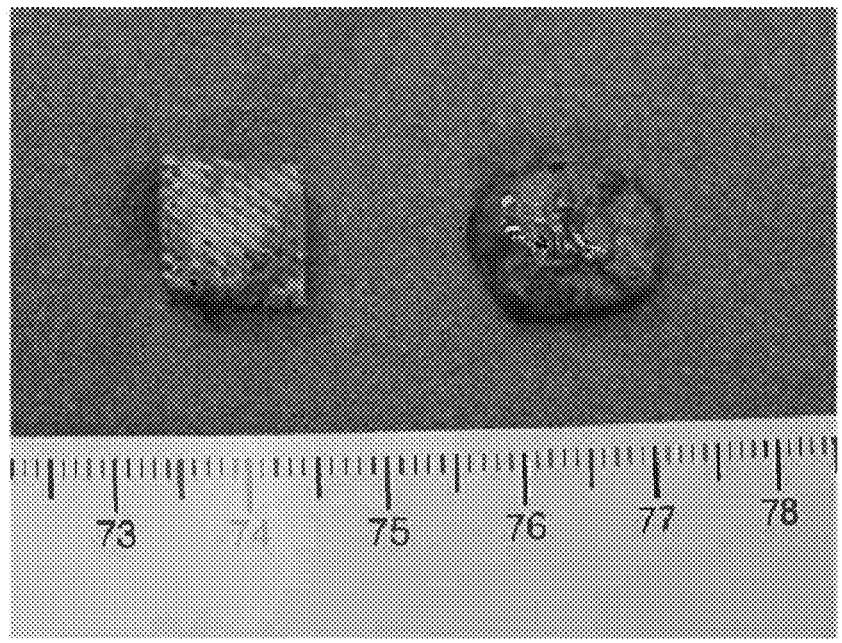
FIGS. 26A and 26B depict sheet-scaffolds constructs in vivo experiment, after 4 weeks depicted in FIG. 26A and after 8 weeks depicted in FIG. 26B.
Figure 26B:
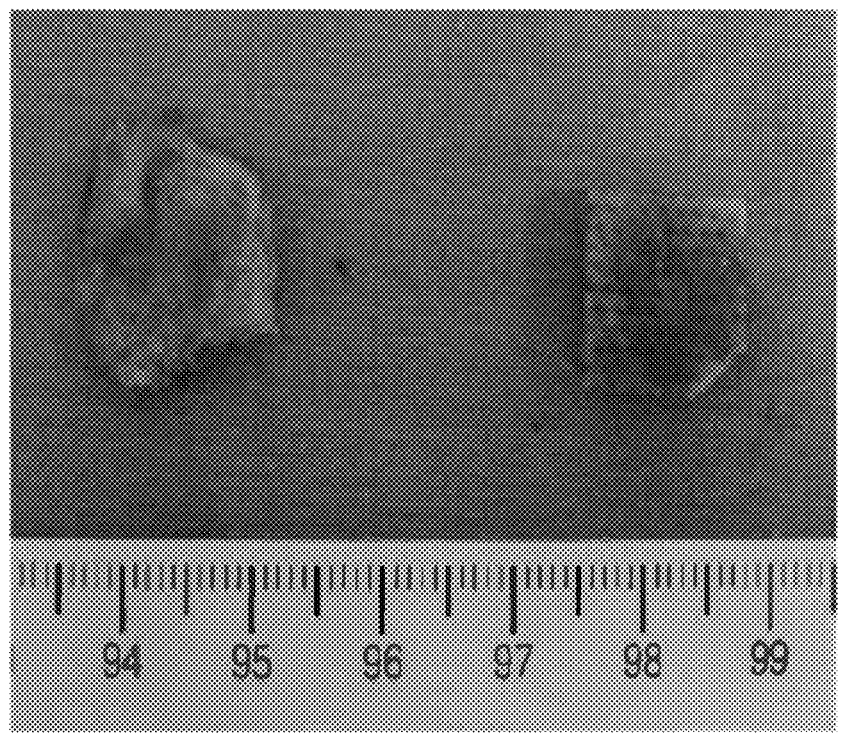
Figure 27A:
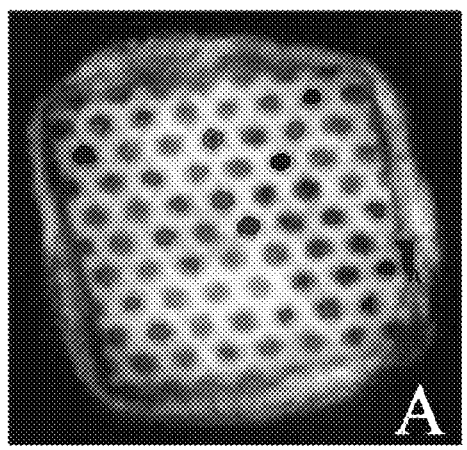
FIGS. 27A, 27B, and 27C depict soft X-ray. Bone formation visualised by X-ray at 25 KV, 6.3 Mas with 4 weeks after implantation in nude rat depicted in FIG. 27A, 8 weeks depicted in FIG. 27B, and after 12 weeks depicted in FIG. 27C.
Figure 27B:
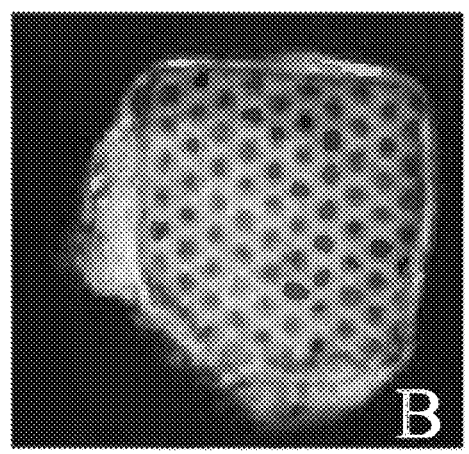
Figure 27C:
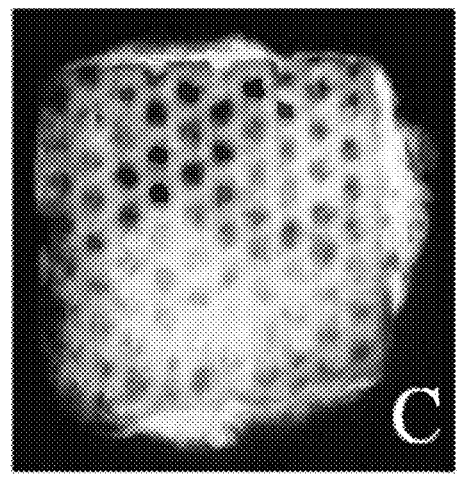
Figure 28:
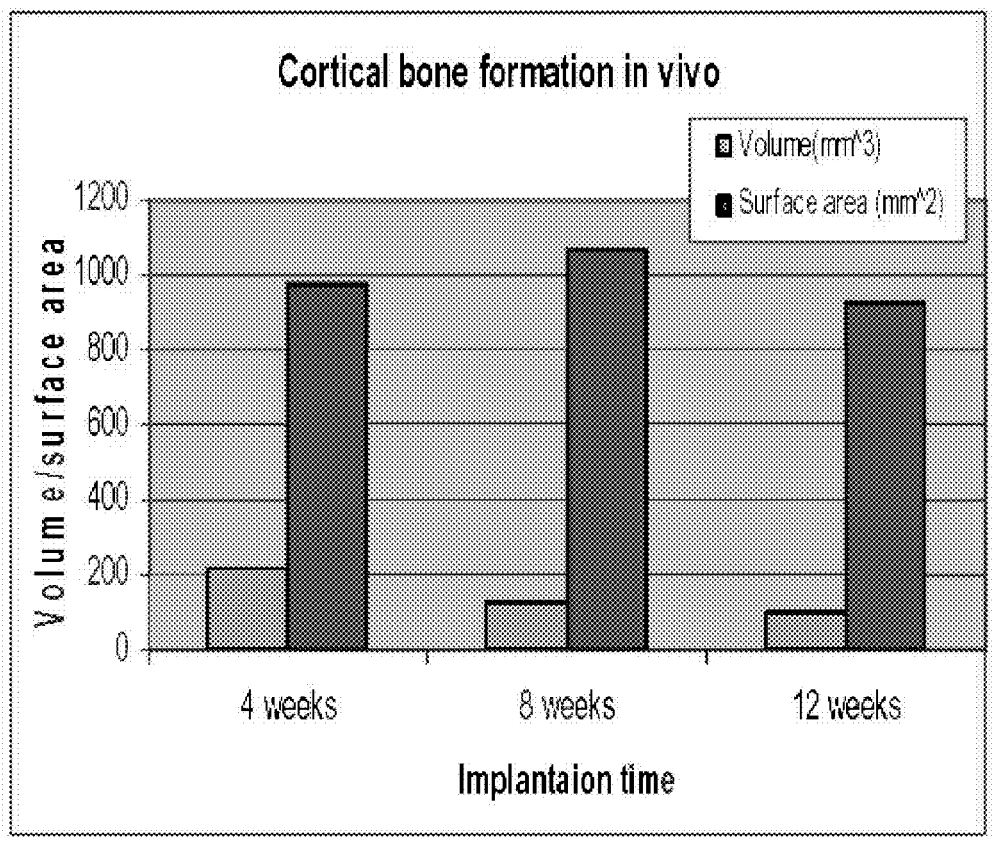
FIG. 28. Micro CT analysis of cortical bone formation. Both the volume and surface of bone formed by implanted sheet-scaffolds constructs decreased over time.
Figure 29A:
FIGS. 29A and 29B depict histology of samples after 4 weeks in FIG. 29A and after 8 weeks depicted in FIG. 29B.
Figure 29B:
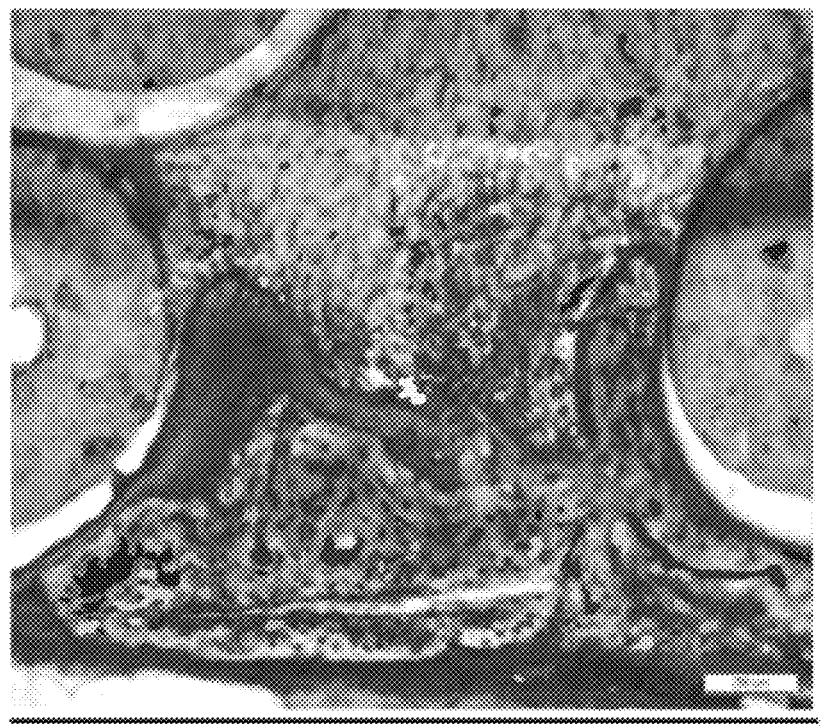
Figure 30A:
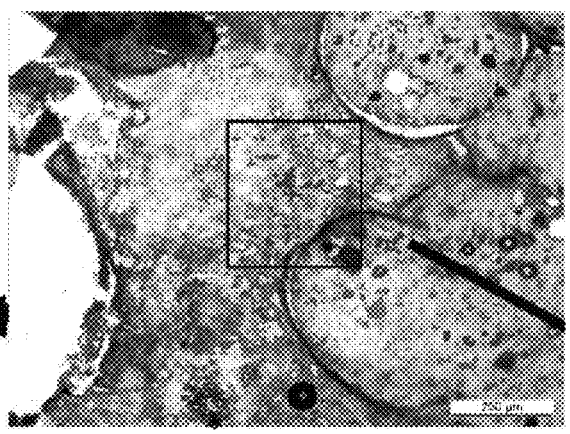
FIGS. 30A, 30B, and 30C depict H/E stain after 8 weeks of implantation at 25× in FIG. 30A, 100× in FIG. 30B, and 400× in FIG. 30C.
Figure 30B:
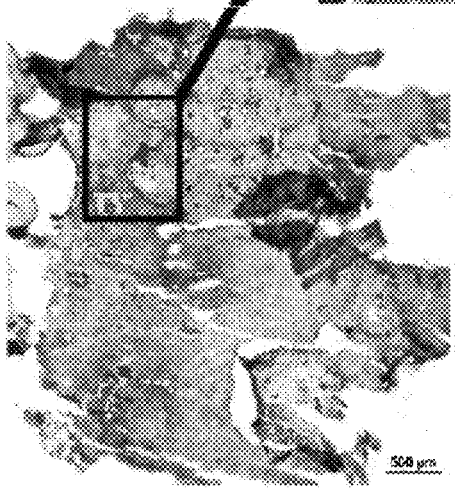
Figure 30C:
Figure 31A:
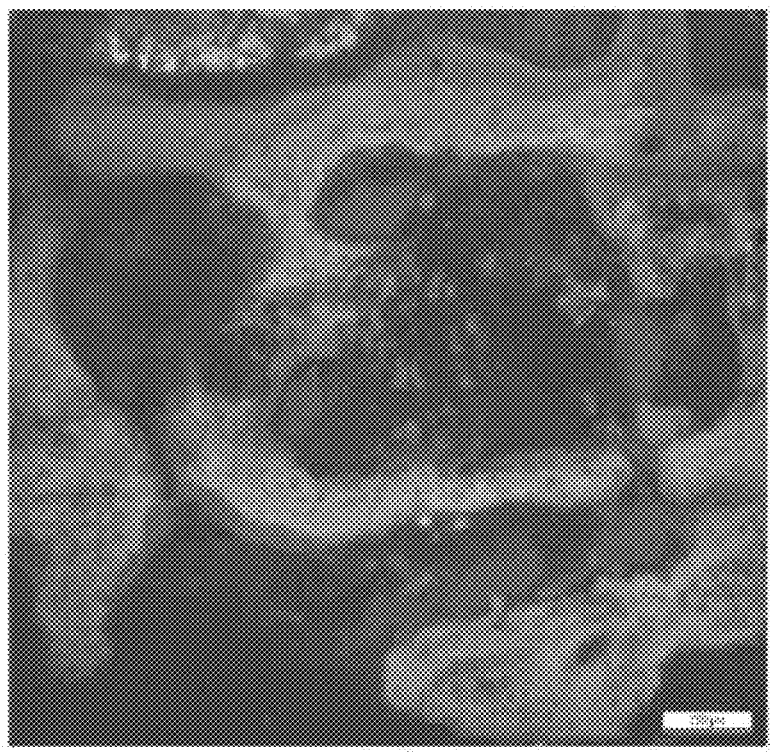
FIGS. 31A and 31B depict fluorescence label cells formed the bone at 4 weeks in FIG. 31A and at 8 weeks in FIG. 31B.
Figure 31B:
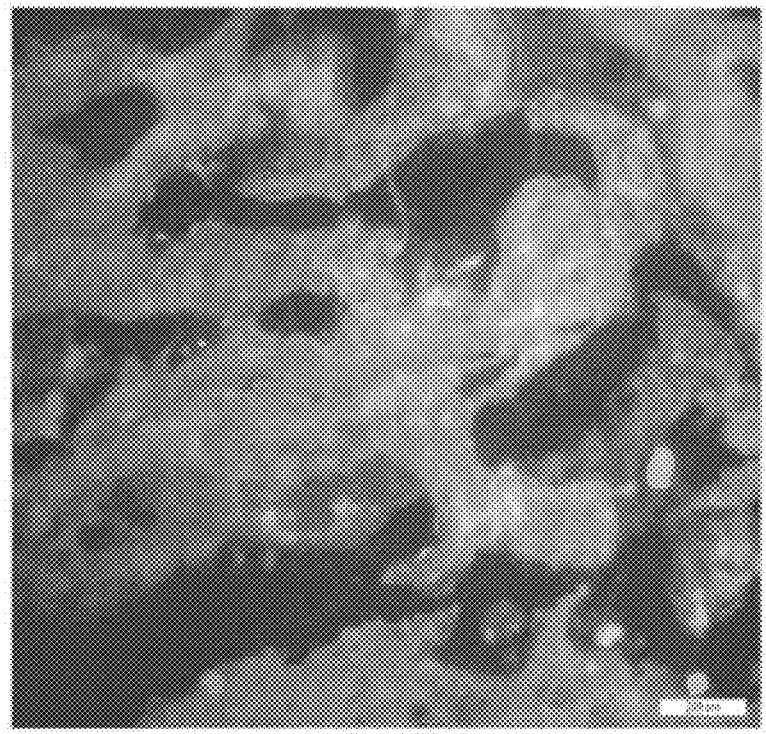

To verify bone formation capability of the engineered constructs, induced and uninduced constructs were implanted in nude rat and taken out after 4, 8, 12 weeks (FIGS. 25, 26). X-ray images in FIG. 27A, B, C shows that there was bone formation in induced constructs. FIG. 8 demonstrates that both the cortical and cancellous bone was formed in the constructs. The cortical bone mainly formed at out side of constructs and cacellous bone formed within constructs through micro CT scan. The volume and surface area of bone formed within constructs decreased over the implantation time (FIGS. 28, 29A,B). To determine the contribution of implanted cells to osteogenesis, we labeled the implanted cells cFDA. FIG. 30A,B shows fluorescence cells mainly habited in the bone area, implying that most of osteoblasts were derived from implanted cells. H/E staining in FIG. 31A,B,C indicated that MSCs in the constructs histological resembled growth plate-like structure at the interface of chondrocytes and bone area. It shows the MSCs within constructs experienced endochondry bone formation process.

Discussion

In this study, we have examined the osteogenesis of hybrid of PMSCs sheet-scaffolds constructs in vitro and in vivo. In vitro results show that MSCs in constructs can grow and differentiate into osteoblasts after osteogenic induction with upregulations of ALP, osteo-related proteins. In vivo data demonstrated that the whole constructs formed both cortical bone and cancellous bone in nude rat after 4 weeks implantation. That means the novel concept in this experiment of MSCs sheet incorporation with TCP-PCL scaffolds may work in bone tissue engineering. The engineered constructs could be candidate in bone substitutes, especially in bear-loading area since the scaffolds in the experiment can sustain higher mechanical force than previous reported scaffolds, which mainly were polymer foams or sheet.

REFERENCES

Broaddus W C, Holloway K L, Winters C J, Bullock M R, Graham R S, Mathern B E, Ward J D, Young H F. Titanium miniplates or stainless steel wire for cranial fixation: a prospective randomized comparison. J Neurosurg. 2002 February; 96 (2):244-7.

Bruijn J D de, van Blitterswijk C A, Davies J E. Initial bone-matrix formation at the hydroxyapatite interface in vivo. *J Biomed Mater Res* 1995; 29: 89.

Caplan A I, Bruder S P. In: Lanza R P. Langer R, Chick W L (eds), Cell and molecular engineering of bone regeneration: Principles of tissue engineering, Academic Press: New York, 1997 p. 603-18.

Dennis Rohner, Dietmar W. Hutmacher, Tan Kim Cheng, Martin Oberholzer, Beat Hammer; In vivo efficacy of bone-marrow-coated polycaprolactone scaffolds for the reconstruction of orbital defects in the pig; J Biomed Mater Res Part B: Appl Biomater 66B: 574-580, 2003.

Dennis J E, Haynesworth S E, Young R G, Caplan A I. Osteogenesis in marrow-derived mesenchymal cell porous ceramic composites transplanted subcutaneously: effect of fibronectin and laminin on cell retention and rate of osteogenic expression. *Cell Transplant* 1992; 1: 23-30.

Du C, Cui F Z, Zhu X D, de Groot K. Three-dimensional nano-HAp/collagen matrix loading with osteogenic cells in organ culture. *J Biomed Mater Res* 1999; 44: 407-414.

Ducy P, Ruiz H, Valerie G, Amy L R, Gerard K; Osf2/Cbfa1: a transcriptional activator of osteoblast differentiation; 1997, Cell, 89:747-54.

Dujovny M, Dujovny N, Vinas F, Park H K, Lopez F. Burr hole cover for ventriculoperitoneal shunts and ventriculostomy: technical note. Neurol Res. 2002 July; 24 (5): 483-4.

Emonds N, Hassler W E. New device to treat chronic subdural hematoma-hollow screw. Neurol Res. 1999 January; 21(1):77-8.

Habal M B, Pietrzak W S. Key points in the fixation of the craniofacial skeleton with absorbable biomaterial. J Craniofac Surg. 1999 November; 10 (6):491-9.

Hutmacher D W, Scaffold design and fabrication technologies for engineering tissues-state of the art and future perspectives. J Biomater Sci Polym Ed. 2001; 12 (1):107-24.

Hutmacher D W, Schantz T, Zein I, Ng K W, Teoh S H, Tan K C, Mechanical properties and cell cultural response of polycaprolactone scaffolds designed and fabricated via fused deposition modeling. J Biomed Mater Res. 2001 May; 55 (2):203-16.

Kobayashi S, Hara H, Okudera H, Takemae T, Sugita K. Usefulness of ceramic implants in neurosurgery. Neurosurgery. 1987 November; 21 (5):751-5.

Koyama J, Hongo K, Iwashita T, Kobayashi S. A newly designed key-hole button. J. Neurosurg. 2000 September; 93 (3):506-8.

Kushida A. M. Yamato, A. Kikuchi and T. Okano, Two-dimensional manipulation of differentiated Madin-Darby canine kidney (MDCK) cell sheets: the noninvasive harvest from temperature-responsive culture dishes and transfer to other surfaces. *J Biomed Mater Res* 54 (2001), pp. 37-46

Linda G, Gail N, Tissue engineering-Current challenges and expanding opportunities; Science; 2002, 295: 1009-1012

Matsumoto K, Kohmura E, Kato A, Hayakawa T. Restoration of small bone defects at craniotomy using autologous bone dust and fibrin glue. Surg Neurol. 1998 October; 50 (4):344-6.

Mikos A G, Sarakinos G, Leite S M, Vacanti J P, Langer R. Laminated three-dimensional biodegradable forms for use in tissue engineering. Biomaterials 1993; 14: 323-330

Miyake H, Ohta T, Tanaka H. A new technique for cranioplasty with L-shaped titanium plates and combination ceramic implants composed of hydroxyapatite and tricalcium phosphate (Ceratite). Neurosurgery. 2000 February; 46 (2):414-8.

Nakashima K, Zhou X, Kunkel G, Zhang Z, Deng J M, Behringer R R, de Crombrugghe B. The novel zinc finger-containing transcription factor osterix is required for osteoblast differentiation and bone formation. Cell. 2002 Jan. 11; 108(1):17-29.

Nicolas L'heureux, Sté phanle Pâquet, Raymond Labbé, Lucie Germain, and François A. Auger; A completely biological tissue-engineered human blood vessel; *FASEB J*. 12, 47-56 (1998).

Nicole IZur Nieden, Grazyna Kempka, Hans J Ahr, In vitro differentiation of embryonic stem cells into mineralized osteoblasts; Differentiation, 2003, 71: 18-27.

Pitt C G, Gratzl M M, Kimmel G L, Surles J, Schindler A. Aliphatic polyesters II. The degradation of poly (DL-lactide), poly (epsilon-caprolactone), and their copolymers in vivo. Biomaterials. 1981, 2 (4): 215-220.

Rochet N, Loubat A, Laugier J P, Hofman P, Bouler J M et al., Modification of gene expression induced in human osteogenic and osteosarcoma cells by culture on a biphasic calcium phosphate bone substitutes. Bone, 2003, 32: 602-10

Schantz J-T, Teoh S H, Lim T C, Endres M. Lam C X F, Hutmacher D W, Repair of Calvarial Defects with Customised Tissue-Engineered Bone Grafts. Part I: Evaluation of Osteogenesis in a 3D Culture System, Tissue Engineering 9 (Sup 1) (2003a): S113-S126.

Schantz J-T, Hutmacher D W, Lam C X F, Brinkmann M, Wong K M, Lim T C, Chou N, Gulberg R E and Teoh S H, Repair of Calvarial Defects with Customised Tissue-Engineered Bone Grafts. Part II: Evaluation of cellular efficiency and efficacy in vivo, Tissue Engineering 9 (Sup 1) (2003b): S127-S139.

Shimizu T, M. Yamato, A. Kikuchi and T. Okano, Two-dimensional manipulation of cardiac myocyte sheets utilizing temperature-responsive culture dishes augments the pulsatile amplitude. *Tissue Eng* 7 (2001), pp. 141-151.

Stendel R, Krischek B, Pietila T A. Biodegradable implants in neurosurgery. Acta Neurochir (Wien). 2001; 143(3): 237-43.

Tessier P. Autogeneous bone grafts taken from the calvarium for facial and cranial applications. Clin Plast Surg. 9: 531, 1982.

Toshimasa u, et al; Transplantation of cultured bone cells using combinations of scaffolds and culture techniques; Biomaterials; 2003, 24:2277-86.

Winkler P A, Herzog C, Weiler C, Krishnan K G. Foreign-body reaction to silastic burr-hole covers with seroma formation: case report and review of the literature. Pathol Res Pract. 2000; 196 (1):61-6.

Yamashima T Cranioplasty with hydroxylapatite ceramic plates that can easily be trimmed during surgery. A preliminary report. Acta Neurochir (Wien). 1989:96(3-4): 149-53.

Yamashina T. Modern cranioplasty with hydroxyapatite button, granules and plates. Neurosurgery. 1993 November; 33 (5):939-40

Iwan Zein. Dietmar W. Hutmacher, Kim Cheng Tan, Swee Hin Teoh. Fused deposition modeling of novel scaffold architectures for tissue engineering applications: Biomaterials 23 (2002) 1169-1185

The invention claimed is:

1. A cranioplasty method for cranial bone tissue regeneration comprising the steps of:
providing a bioabsorbable cranioplasty plug implant consisting of a top-hat shape and comprising: a first portion having a first surface; and a second portion having a second surface opposite to the first surface, the second surface extending outwardly from the first portion, wherein the first surface has an area smaller than an area of the second surface, and wherein the first portion and the second portion are formed from expandable material, wherein the expandable material is prepared by layering polycaprolactone (PCL) filaments layer by layer;
inserting the first portion of the cranioplasty plug implant into a defect or gap of a cranial bone, the second portion of the cranioplasty plug implant engaging an external surface of the bone surrounding the defect or gap; and
allowing the cranioplasty plug implant to contact-body fluids, thereby expanding the size of the cranioplasty plug implant so that the plug snap fits into the defect or gap without requiring any additional means for fixing the cranioplasty plug implant to the external surface of the bone surrounding the defect or gap.

2. The method according to claim 1, wherein the cranioplasty plug implant is formed from a porous material allowing the bone cells to penetrate into the cranioplasty plug implant and to regenerate the bone tissue.

3. The method according to claim 1, wherein the cranioplasty plug implant and the bone defect or gap have an initial tolerance of less than 1 mm.

4. The method according to claim 3, wherein the initial tolerance is less than 0.5 mm.

5. The method according to claim 3, wherein the initial tolerance is less than 0.2 mm.

6. The method according to claim 1, further comprising placing a catheter into an opening of the plug implant for performing drainage.

7. The method according to claim 1, wherein the method for cranial bone tissue regeneration is a cosmetic restoration of undesirable osseous gaps.

8. The method according to claim 1, wherein the cranioplasty plug implant further comprises seeding cells on a bioabsorbable scaffold of the plug implant.

9. The method according to claim 8, wherein the cells are stem cells.

10. The method according to claim 8, wherein the cells are mesenchymal stem cells.

11. The method according to claim 1, wherein the layers of the PCL filaments have an orientation of 0 degree, 60 degrees and 120 degrees.

* * * * *